(12) United States Patent
Nakajima et al.

(10) Patent No.: US 8,025,842 B2
(45) Date of Patent: Sep. 27, 2011

(54) APPARATUS AND METHOD FOR PREPARING SLICED SPECIMEN

(75) Inventors: Daisuke Nakajima, Neyagawa (JP); Yoshihiko Isagawa, Neyagawa (JP); Hiroaki Iida, Neyagawa (JP); Toshiyuki Murakami, Neyagawa (JP)

(73) Assignee: Kurashiki Boseki Kabushiki Kaisha, Okayama (JP)

( * ) Notice: Subject to any disclaimer, the term of this patent is extended or adjusted under 35 U.S.C. 154(b) by 1041 days.

(21) Appl. No.: 11/902,357

(22) Filed: Sep. 20, 2007

(65) Prior Publication Data

US 2008/0072723 A1    Mar. 27, 2008

(30) Foreign Application Priority Data

Sep. 21, 2006  (JP) ................................. 2006-256243
Sep. 21, 2006  (JP) ................................. 2006-256246
Sep. 21, 2006  (JP) ................................. 2006-256253

(51) Int. Cl.
*G01N 21/00* (2006.01)

(52) U.S. Cl. ................ 422/65; 422/64; 422/66; 422/67; 436/180; 83/367; 83/421

(58) Field of Classification Search ............. 422/64–67; 436/180; 83/367, 421
See application file for complete search history.

(56) References Cited

U.S. PATENT DOCUMENTS 5,461,953 A   10/1995 McCormick
6,568,307 B1   5/2003 Gunther et al.

FOREIGN PATENT DOCUMENTS

| EP | 0 544 181 A1 | 6/1993 |
| EP | 1 037 033 A2 | 9/2000 |
| JP | 11-153521 A | 6/1999 |
| JP | 2004-28910 A | 1/2004 |
| JP | 3656005 B2 | 3/2005 |
| JP | 3745554 B2 | 12/2005 |

OTHER PUBLICATIONS

Partial European Search Report issued on Jan. 27, 2010 in corresponding European Patent Application No. 07 01 8521.

*Primary Examiner* — Jyoti Nagpaul
(74) *Attorney, Agent, or Firm* — Birch, Stewart, Kolasch & Birch, LLP

(57) ABSTRACT

Sliced specimens can be automatically and continuously prepared and burdens of an operator can be reduced while accuracy required for the sliced specimen is maintained. The sliced specimen is prepared by relatively moving a specimen block transfer section and a cutter, and when a slicing operation to adjust the height position of the specimen block is continuously performed so that the cutting surface of the specimen block is located at a sliceable position, the cutter is moved so that a contacting area of a blade edge of the cutter that firstly contacts the specimen block after the height position adjustment is sequentially changed, every time previously set number of times of slicing operation is completed. Thereafter, the height position of the blade edge of the cutter after the change is measured by a detector, and based on the measurement information of the detector, the sliceable position is corrected and the slicing operation is resumed.

9 Claims, 20 Drawing Sheets

APPARATUS AND METHOD FOR PREPARING SLICED SPECIMEN

BACKGROUND OF THE INVENTION

1. Field of the Invention

The present invention relates to an apparatus and a method for preparing a sliced specimen used in physical and chemical sample analysis, microscopic observation of a biotic sample, and the like.

2. Description of the Related Art

Conventionally, a microtome is generally known as an apparatus for preparing a sliced specimen used in physical and chemical sample analysis, microscopic observation of a biotic sample, and the like. The microtome is an apparatus for slicing a surface layer portion of a specimen block by using a manually-operated cutter, the specimen block being obtained by embedding a specimen such as a biotic sample in an embedding substance such as paraffin.

A thin slice sliced by the microtome is extremely thinly sliced, and therefore is in a curling state. In order to stretch this thin slice, the thin slice is put in a bath filled with a liquid for stretch, such as water or hot water, by using a brush or paper, for example. When the thin slice is stretched by the liquid in the bath, the thin slice in the bath is scooped by using the brush and paper, and is applied to a slide by using an adhesive liquid (such as water). Alternatively, the slide is put in the bath, the thin slice in the liquid is directly scooped and is applied to the slide.

The thin slice disposed on the slide tightly adheres to the slide by further stretching wrinkles and the like by heating the slide. The thin slice adhering to the slide becomes tightly fixed to the slide with evaporation of the adhesive liquid, and is used as a sliced specimen for tissue observation.

The preparation work of the sliced specimen by using the microtome as described above is conventionally performed manually by an operator, and requires much time and labor. Several days are usually required for processing several dozens of specimen blocks even by an operator skilled in using the microtome, and also this is a repetition of the same operation. Therefore, the operator has to bear an excessive burden physically and mentally. In addition, a plurality of slices are put in the bath, thus involving a problem of contamination between specimens through the liquid.

Further, although a thickness required for the sliced specimen is different depending on the specimen, an extremely thin slice in a range, e.g., from 3 μm to 10 μm is required, and high uniformity is also required. Meanwhile, in the conventional method using the microtome, height position aligning of the specimen blocks and position (height) adjustment of cutters are visually performed by the operator. Therefore, there is a variation in accuracy (thickness and uniformity) of the sliced specimens depending on the operator, and even in a case of the same operator, a variation in the accuracy of the sliced specimens occurs due to a fatigue degree of the operator. Therefore, an apparatus capable of reducing the burden of the operator and reducing deterioration of the accuracy of the sliced specimen is required.

Japanese Laid-Open Patent Publication No. 2004-28910) discloses an apparatus for sticking a sliced specimen that sticks a specimen onto the surface of a slide, wherein the sliced specimen is obtained by slicing a specimen block in which a sample is embedded in paraffin and the like by a cutter, this sliced specimen is carried by a carrier tape, thereafter the carrier tape is run to send the sliced specimen to a front face of the slide, and next the carrier tape is made in tight contact with the surface of the slide, thereby sticking the specimen to the surface of the slide.

In this apparatus, the specimen block is transferred with a surface layer portion of the specimen block contacting a cutting blade of the cutter, and the surface layer portion of the specimen block is sliced, to thereby prepare the sliced specimen. In addition, this apparatus is operated in such a way that by controlling the running of the carrier tape, the slice carried by the carrier tape is moved to the front face of the slide coated with an adhesive liquid, thereafter the thin slice is stuck onto the slide by putting the carrier tape closer to the surface of the slide, and the slide is heated to stretch the wrinkles of the slice, which is then transferred to the outside of the apparatus.

Incidentally, in the aforementioned apparatus, the sample embedded in this specimen block is sliced along a transfer direction of the specimen block, and therefore face preparation for a top face of the specimen block is important. Namely, when the specimen block is inclined at a predetermined angle, the thickness of the sliced specimen is thereby influenced, thus making it impossible to prepare the sliced specimen with a uniform thickness.

Further, Japanese Patent No. 3656005 discloses a method of preparing a specimen by adjusting an inclination angle of the specimen when using a microtome. In this document, the surface of the specimen block formed with a flat surface in advance is pressed against a reference surface, and a face preparation for the specimen block is performed.

Generally, when the surface layer portion of a specimen block is sliced by a cutter, paraffin and the like is stuck to the blade edge of the cutter, thereby deteriorating the accuracy of slicing of the sliced specimen to be prepared next. Particularly, when the specimen block is continuously sliced by using the same area of the blade edge of the cutter, a cutting quality of this area of the cutter is gradually lowered, thus significantly deteriorating the accuracy of the sliced specimen.

In order to solve the above-described problem, Japanese Laid-Open Patent Publication No. 11-153521 discloses a microtome by which a cutter is moved to automatically change the contacting area, so that the contacting area where the blade edge of the cutter firstly contacts the surface layer portion of a specimen block does not concentrate on the same area, when the surface layer portion of the specimen block is continuously sliced. According to the apparatus of Japanese Laid-Open Patent Publication No. 11-153521, by moving the cutter so as to automatically and suitably change the contacting area, it is possible to reduce the burden of the operator, such as an replacing work of the cutter or a changing work of an attachment position of the cutter, and also it is possible to reduce the deterioration of the accuracy of the sliced specimen by constantly maintaining a good cutting quality of the cutter.

However, in the aforementioned apparatus of Japanese Laid-Open Patent Publication No. 11-153521, a shift occurs in some cases in height position of the blade edge of the cutter that contacts the specimen block before and after the movement of the cutter, due to wear by friction between the cutter and a holder holding the cutter, caused by repeated movement of the cutter. Also, a difference occurs in height position of the blade edge of the cutter that contacts the specimen block, due to individual variability of the cutter and attachment adjustment of the cutter to the holder (for example, a fastening adjustment of a screw when the cutter is screw-fixed to the holder).

Therefore, in the aforementioned apparatus of Japanese Laid-Open Patent Publication No. 11-153521, when the shift occurs during automatically and continuously slicing the sliced specimen, there occurs such a failure that missing in slicing operation of the cutter occurs, or the thickness of the sliced specimen becomes smaller or larger than the thickness required for the sliced specimen, or the blade sticks into the specimen block to damage the specimen block, thus deteriorating the accuracy of the sliced specimen. In order to solve such a defect, for example, the operator must always monitor the operation of the apparatus for preparing the sliced specimen, and when the accuracy of the sliced specimen is deteriorated or the shift occurs in the height position of the blade edge of the cutter that contacts the specimen block, the operator must perform the work such as stopping the apparatus and adjusting the height position of the cutter or the specimen block, and the operator's burden is further increased.

Further, the apparatus disclosed in Japanese Laid-Open Patent Publication No. 2004-28910 is adapted to transfer a thin slice to the outside of the apparatus every time one piece of the thin slice is stuck to the slide. Accordingly, when a large number of thinly sliced specimens are prepared, the number of slides are also increased, thus involving a problem that a drying space is increased and a cost is accordingly increased.

In addition, quantity of work of a staining work, being the next step, is large amount, thus involving a problem of inviting a wasteful amount of staining reagent and deterioration in efficiency of experimental evaluation.

Accordingly, in order to solve the above-described issues, a technical object of the present invention is to provide an apparatus and a method for preparing the sliced specimen, for automatically sticking the thin slice to the slide.

SUMMARY OF THE INVENTION

In order to achieve the above-described object, the present invention includes several aspects as follows.

A first aspect provides a sliced specimen preparing apparatus comprising:

a specimen block transfer section capable of adjusting a height position of a specimen block, for transferring the specimen block;

a cutter section with a cutter movable in an extending direction of a blade;

a detector for detecting a position of the blade of the cutter in a direction orthogonal to a transfer direction of the specimen block;

a carrier tape guide section for carrying and moving a thin slice of the specimen block sliced by the cutter on a surface of a carrier tape;

a slice sticking part for making a portion of the carrier tape carrying the thin slice close to a surface of a slide and making the thin slice carried by the carrier tape transfer to the surface of the slide; and an operation controller performing operation control of the specimen block transfer section, the cutter section, the detector, the carrier tape guide section, and the slice sticking part and continuously preparing a sliced specimen obtained by automatically and continuously slicing a surface layer portion of the specimen block by the cutter and making the thin slice transfer to the slide, wherein the operation controller controls such that, by relatively moving the specimen block transfer section and the cutter of the cutter section, the surface layer portion of the specimen block is sliced by the cutter to prepare the sliced specimen, and the height position of the specimen block is adjusted such that a cutting surface after the slicing of the specimen block is located at a sliceable position, and this slicing operation is continuously performed, at this time, every time a previously set number of times of the slicing operation is completed, the cutter is moved in the extending direction of the blade such that a contacting area of a blade edge of the cutter firstly contacting the specimen block after the adjustment of the height position is sequentially changed, and thereafter the height position of the blade edge of the cutter after the change in a thickness direction of the blade is measured by the detector, and based on measurement information of the detector, the sliceable position is corrected such that the sliceable position is aligned to a position apart from the height position of the blade edge of the cutter after the change, by a thickness of the sliced specimen in the thickness direction of the blade, and then the slicing operation is resumed.

A second aspect provides the sliced specimen preparing apparatus of the first aspect, wherein the cutter section includes a nozzle for discharging compressed air toward the blade edge of the cutter and an air supply section for supplying the compressed air to the nozzle; and the operation controller controls the cutter section such that the compressed air is blown against the blade edge of the cutter contacting the specimen block after preparing the sliced specimen by the cutter, in each of the slicing operation.

A third aspect provides a sliced specimen preparing apparatus, comprising:

a transfer section for transferring in an X-axial direction a block placement table, the block placement table being configured such that an inclination angle of a specimen block having a flat and smooth top face relative to an XY orthogonal two-axial directions and a Z-axis directional height position are changeable;

a line sensor provided in a transfer route of the block placement table by the transfer section, and having a projector and a light receiver disposed opposite to each other in the Y-axial direction and emitting light having a width in a Z-axial direction;

a cutter extending in the Y-axial direction to slice a surface layer portion of the specimen block transferred in the X-axial direction by the transfer section;

a carrier tape guide section for moving a thin slice of the specimen block sliced by the cutter while carrying the thin slice on a surface of a carrier tape;

a slice sticking part for making a portion of the carrier tape carrying the thin slice close to a surface of a slide, and making the thin slice carried by the carrier tape transfer onto the surface of the slide; and an operation controller performing operation control of the specimen block transfer section, the cutter section, the detector, the carrier tape guide section, and the slice sticking part, automatically and continuously slicing the surface layer portion of the specimen block by the cutter, and transferring the sliced surface layer portion onto the slide to continuously prepare a sliced specimen, wherein the operation controller performs control such that the transfer section is driven such that an approximately X-axis directional intermediate position of the specimen block is aligned with a set position of the line sensor, a received light amount of the line sensor is detected while adjusting an inclination direction of the block placement table in the Y-axial direction to fix the Y-axis directional inclination angle of the specimen block at an angle at which the received light amount of the line sensor becomes maximum, the transfer section is driven such that the block placement table is moved back and forth in the X-axial direction by a predetermined amount, to detect the received light amount of the line sensor at the position, and the X-axis directional inclination angle of the specimen block is calculated based on the predetermined amount of movement of the specimen block in the X-axial direction and the information on the received light amount of the line sensor at each position, and the inclination angle of the block placement table is adjusted such that the calculated X-axis directional inclination angle makes a predetermined angle with respect to an XY plane.

A fourth aspect provides the sliced specimen preparing apparatus of the third aspect, wherein after the operation controller drives the transfer section such that the approximately X-axis directional intermediate position of the specimen block is aligned with the set position of the line sensor, and before the inclination direction of the specimen block is adjusted in the Y-axial direction, the operation controller drives the transfer section such that a height position of the block placement table in the Z-axial direction is adjusted such that the received light amount of the line sensor is set to be a predetermined amount by light shielding by the specimen block.

A fifth aspect provides the sliced specimen preparing apparatus of the third aspect, wherein the operation controller adjusts the inclination angle of the transfer section such that the calculated X-axis directional inclination angle is parallel to the XY plane.

A sixth aspect provides a sliced specimen preparing apparatus for sticking a thin slice obtained by slicing a surface layer portion of a specimen block and transferred while being adsorbed on a carrier tape, to a slide to which an adhesive liquid is applied, the apparatus comprising:

a slide supply section capable of storing the slide in an unused state and carrying out the slide one by one;

a first transfer section extending from the slide supply section in a direction crossing a traveling track of the carrier tape;

an adhesive liquid application section for applying the adhesive liquid onto a predetermined position of the slide, at a place on the first transfer section located between a sticking position, to which the thin slice is stuck, on the slide transferred by the first transfer section and the slide supply section;

a slice sticking part for making the thin slice transfer onto the slide by performing alignment such that the thin slice adsorbed on the carrier tape is made to face the sticking position on the slide transferred by the first transfer section, and by making the carrier tape come into contact with the slide;

a second transfer section provided in parallel to the first transfer section, for transferring the slide transferred by the first transfer section in an opposite direction to the transfer direction of the first transfer section;

a returning transfer section provided in communication with the second transfer section, for supplying the slide transferred by the second transfer section to the first transfer section again;

a carrying-out section provided in communication with the second transfer section, for carrying out the slide transferred by the second transfer section to the outside of the apparatus; and a switch section for switching the transfer direction of the slide transferred by the second transfer section toward one of the returning transfer section and the carrying-out section.

A seventh aspect provides the sliced specimen preparing apparatus of the sixth aspect, wherein the second transfer section includes a heating and heat reserving section for heating and heat-preserving the slide.

An eight aspect provides the sliced specimen preparing apparatus of the sixth aspect, wherein the adhesive liquid application section includes a spray nozzle for applying the adhesive liquid in a misty state onto the slide transferred by the first transfer section.

A ninth aspect provides the sliced specimen preparing apparatus of the sixth aspect, wherein the adhesive liquid application section includes an adhesive liquid storage tank storing the adhesive liquid, and a drop nozzle for dropping the adhesive liquid onto the slide provided at a position lower than the adhesive liquid storage tank, and the adhesive liquid application section is provided on an upper side of the first transfer section with a drop distance secured such that a droplet dropped from the drop nozzle impinges on the slide and is diffused.

A tenth aspect provides a sliced specimen preparing method, for sticking thin slices to a slide by using a sliced specimen preparing apparatus the sticks the thin slice transferred in a state of being adsorbed on a carrier tape and prepared by slicing a surface layer portion of a specimen block, to the slide to which an adhesive liquid is applied, the method comprising:

applying the adhesive liquid to a first slice sticking position, being any position on the slide, in a first transfer section that transfers the slide in a direction crossing a traveling track of the carrier tape on a first transfer section;

controlling a travel amount of the carrier tape and a transfer amount of the slide on the first transfer section, to perform alignment such that the thin slice faces the first slice sticking position;

making the thin slice transfer onto the first slice sticking position of the slide;

supplying the slide from the first transfer section to a second transfer section having a heating unit, and stretching a wrinkle of the thin slice and making the thin slice tightly adhering to the slide, while transferring the slide in an opposite direction to the transfer direction of the first transfer section;

applying the adhesive liquid to a second slice sticking position on the slide different from the first slice sticking position, while transferring the slide on the first transfer section after disposing the slide from the second transfer section to the first transfer section;

controlling the travel amount of the carrier tape and the transfer amount of the slide on the first transfer section, to perform alignment such that a thin slice faces the second slice sticking position; and making the thin slice transfer onto the second slice sticking position of the slide thereby sticking a plurality of the thin slices to the slide.

According to the first aspect, the height position of the specimen block is adjusted such that a cutting surface after slicing the specimen block is located at a sliceable position in one slicing operation. Accordingly, the specimen block is always adjusted to be located at the same sliceable position, thus making it possible to prevent deterioration of accuracy required for the sliced specimen, due to a positional shift of the specimen block from the sliceable position.

In addition, every time the slicing operation of the number of times set in advance is completed, the cutter moves in an extending direction of the blade, so that the position of the blade edge of the cutter that firstly contacts the specimen block after the adjustment of the height position is sequentially changed. Accordingly, the contacting area of the blade edge of the cutter used in slicing the specimen block can be made different, thus making it possible to maintain the cutting quality of the cutter in a good state. Moreover, an entire part of the blade edge of the cutter can be used, thus making it possible to reduce the loads of the operator by reducing the number of replacement of cutter.

Further, according the first aspect of the present invention, every time the cutter movement in the extending direction of the blade is completed, the height position of the blade edge of the cutter after the change is measured by the detector, and based on the measurement information of the detector, the sliceable position in the thickness direction of the blade is corrected. Accordingly, even when a shift occurs before and after the movement of the cutter in the height position of the blade edge of the cutter that contacts the specimen block, the shift can be corrected.

Therefore, according to the first aspect of the present invention, when the slicing operation is performed, the specimen block is moved so as to always maintain a distance in the thickness direction of the blade by the thickness of the sliced specimen at the blade edge of the cutter that contacts the specimen block, thus making it possible to prepare the sliced specimen automatically and continuously, and to reduce the burden of the operator while maintaining the accuracy required for the sliced specimen.

In addition, according to the second aspect of the present invention, the compressed air is blown onto the blade edge of the cutter. Accordingly, even if paraffin and the like adheres to the blade edge of the cutter, the paraffin and the like can be blown off by the compressed air, thus making it possible to reduce the burden of the operator while reducing the deterioration of the cutting quality and maintaining the accuracy required for the sliced specimen.

According to the third aspect of the present invention, by using the line sensor having the projector and the light receiver to detect a light amount shielded by the specimen block, the inclination angle of the specimen block can be measured, thus making it possible to perform surface preparation in a non-contacting manner on the specimen block. In addition, the inclination angle with respect to a projection direction of the line sensor is adjusted such that a portion where the amount of light received of the line sensor becomes maximum is detected in consideration of the specimen block which is semi-transparent made of paraffin. Therefore, the inclination angle in the direction can be made to be parallel to the projection direction.

Further, the adjustment of the inclination angle in a direction crossing the projection direction of the line sensor cannot be performed only with the amount of light received by the specimen block. Therefore, by shifting the position of the specimen block and detecting the received light amount at each of the positions, the inclination angle of the specimen block can be calculated, and thus the inclination angle can be calculated.

According to the fourth aspect of the present invention, the specimen block is disposed so as to be located at a previously defined height direction position, thus making it possible to facilitate calculation control based on the received light amount of the line sensor.

According to the fifth aspect of the present invention, the X-axis directional inclination angle is made parallel to the XY plane, and when the transfer section is driven so that the block placement table is moved back and forth in the X-axial direction by a predetermined amount, the received light amount of the line sensor is detected and by setting this received light amount at the same value, adjustment control of the inclination angle can be facilitated.

According to the sixth aspect of the present invention, the first transfer section is extended in the direction crossing the travel track of the carrier tape. Therefore, by adjusting the travel position of the carrier tape, a corresponding position of the slide transferred on the first transfer section and the thin slice carried by the carrier tape can be changed. Accordingly, the thin slice can be moved so as to face the adhesive liquid applied at a predetermined position by the adhesive liquid applying device, and the thin slice can be stuck to a predetermined position of the slide.

In addition, by the second transfer section, the slide, to which the thin slice is stuck, is transferred in the direction opposite to the transfer direction of the first transfer section, and by the returning transfer section, the slide is returned to the first transfer section, thus making it possible to transfer the slide to the position where the adhesive liquid applying device for reapplication and the carrier tape are faced with each other. Thus, by re-application of the adhesive liquid to stick the thin slice from the carrier tape to the slide, a plurality of slices can be stuck onto one sheet of the slide.

According to the seventh aspect of the present invention, the heating part is provided in the second transfer section, thus making it possible to prevent regeneration of wrinkles by cooling the slide during transfer of the second transfer section.

According to the eighth aspect of the present invention, the adhesive liquid is made misty and can be applied thinly on an entire body of the slide. Accordingly, for example, even in a case of the slide to which the thin slice is stuck, the adhesive liquid is thinly applied in the form of a fine mist, and a positional shift of the slice cannot be thereby caused, thus making it possible to facilitate the application of the adhesive liquid onto the slide, irrespective of the position of sticking the thin slice to the slide.

According to the ninth aspect of the present invention, the dropping nozzle is provided at a position lower than the adhesive liquid storage tank, thus making it possible to drop a predetermined amount of adhesive liquid by gravitational force. Namely, only by opening/closing a flow passage between the adhesive liquid storage tank and the dropping nozzle, discharge control of the adhesive liquid can be performed, thus making it possible to facilitate the operation. In addition, a drop distance between the dropping nozzle and the slide is a predetermined amount or more, and the adhesive liquid impinges on the slide to be diffused, thus making it possible to facilitate the application of the adhesive liquid on the surface of the slide.

BRIEF DESCRIPTION OF THE DRAWINGS

These and other aspects and features of the present invention will become clear from the following description taken in conjunction with the preferred embodiments thereof with reference to the accompanying drawings, in which.

DETAILED DESCRIPTION OF THE PREFERRED EMBODIMENTS

Figure 1:
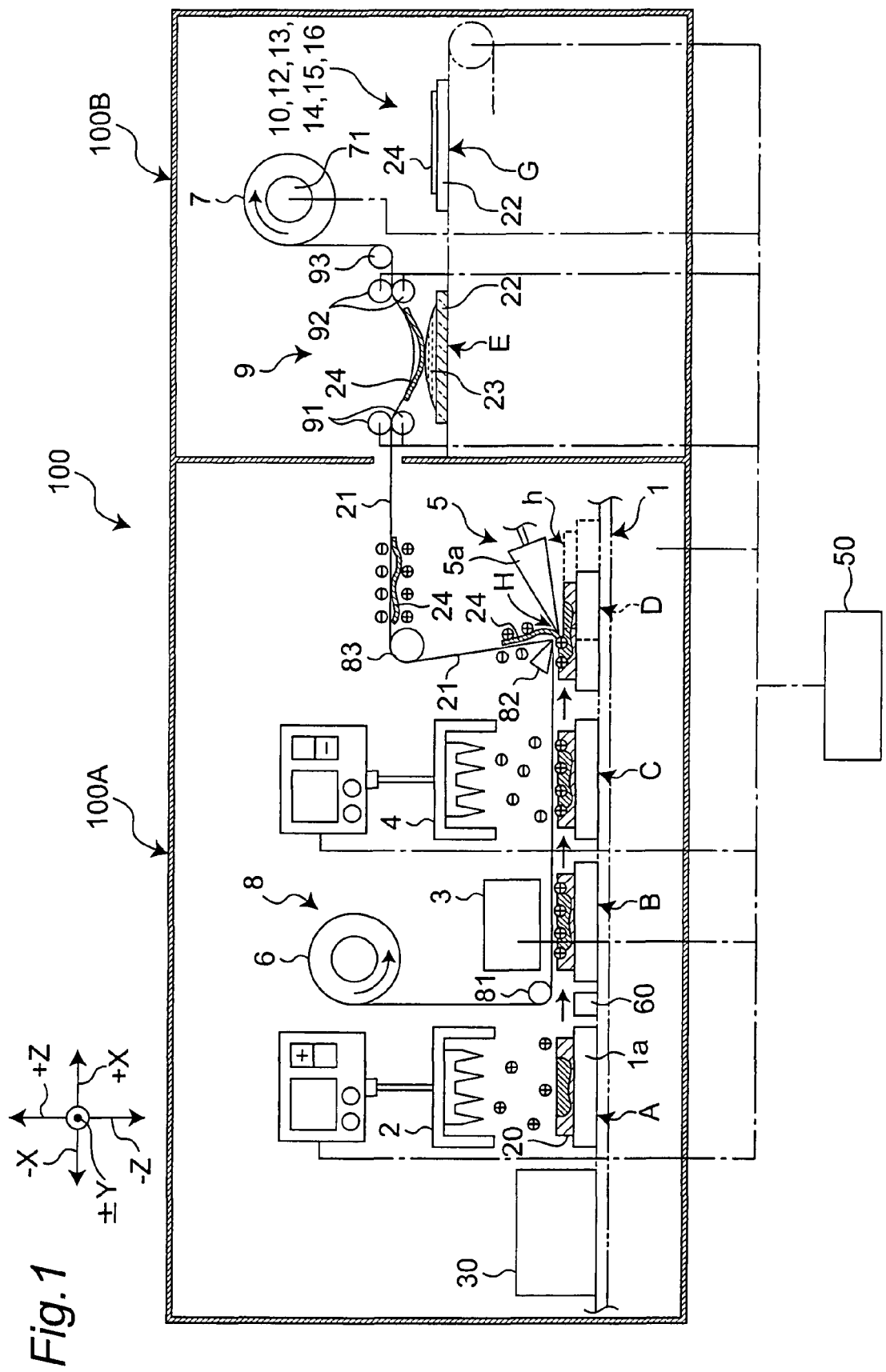
FIG. 1 is a front view showing a schematic structure of a sliced specimen preparing apparatus according to an embodiment of the present invention.

Before the description of the present invention proceeds, it is to be noted that like parts are designated by like reference numerals throughout the accompanying drawings. A first embodiment of the present invention will be described in detail hereinafter with reference to the drawings.

Figure 2:
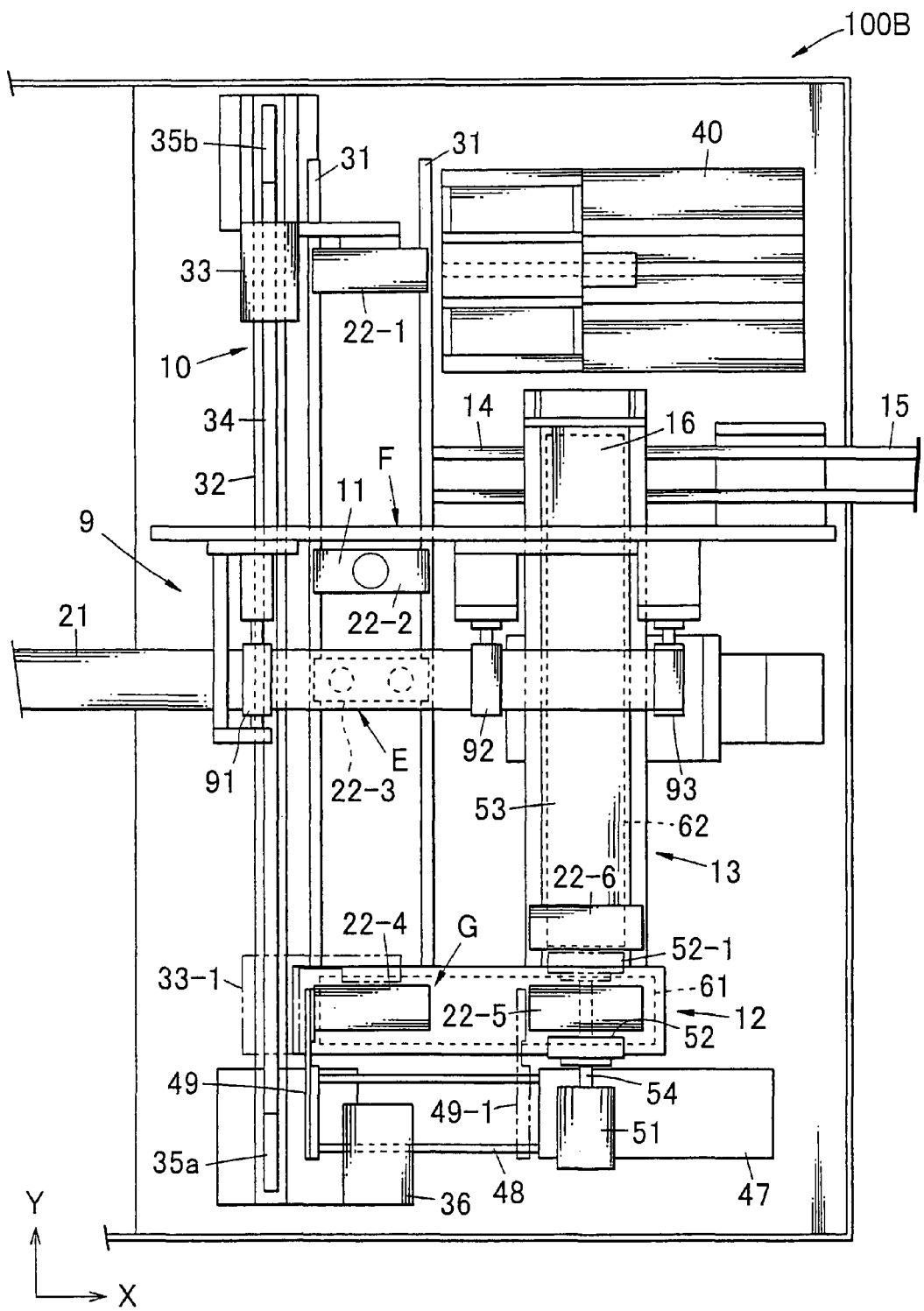
FIG. 2 is a plan view showing a schematic structure in a specimen sticking chamber of the sliced specimen preparing apparatus of FIG. 1.

First, an entire structure and an operation of a sliced specimen preparing apparatus 100 according to an embodiment of the present invention will be described. FIG. 1 is a front view showing a schematic structure of the sliced specimen preparing apparatus 100 according to the embodiment of the present invention. FIG. 2 is a plan view showing the schematic structure of a specimen sticking chamber of the sliced specimen preparing apparatus of FIG. 1.

In FIG. 1, the sliced specimen preparing apparatus 100 includes a specimen preparing chamber 100A in which a series of constitutional parts are disposed to prepare a sliced specimen 24 by slicing a specimen block 20; and a specimen sticking chamber 100B in which a series of constitutional parts are disposed to firmly stick the sliced specimen 24 sliced in the specimen preparing chamber 100A to a slide 22.

As an example of the specimen block 20 subjected to slicing processing in the sliced specimen preparing apparatus 100, a specimen block obtained by embedding a specimen such as a biotic sample in an embedding substance such as paraffin is used. Such a specimen block 20 is easily scratched or deformed at the cutting surface when its surface layer portion is cut in a dry state, and also is easily expanded or contracted by a delicate change in temperature and humidity, thus involving a problem that irregularity in thickness of the thin slice is easily generated during the slicing processing. Therefore, the temperature and the humidity of the inside of the specimen preparing chamber 100A is adjusted to be maintained at a constant temperature (such as 25° C.) and a constant high humidity (such as 65% or more) by an air conditioner and a humidifier (not shown). It is noted that the aforementioned temperature and humidity may be suitably set depending on the kinds of the specimen and the embedding substance.

In the specimen preparing chamber 100A, a specimen storage section 30, a specimen block transfer section 1, a first charger 2, a cooler 3, a second charger 4, a cutter section 5, a supply reel 6, and a carrier tape guide section 8 are disposed.

In the specimen sticking chamber 100B, a take-up reel 7, a slice sticking part 9, a slide transfer section 10, an adhesive liquid application section 11, a spreading section 12, and a slide storage section 40 are disposed.

A controller 50 as will be described later is connected to each constitutional part provided in the specimen preparing chamber 100A and the specimen sticking chamber 100B, and a control signal from the controller 50 is received and the operation is suitably performed.

The specimen block transfer section 1 is configured so that a specimen block placement table 1a that holds the specimen block 20 thereon can be reciprocally transferred between positions A to D. The specimen block transferred by the specimen block transfer section 1 is stored in the specimen storage section 30 that stores a plurality of specimen blocks in the same temperature/humidity environment as those in the specimen preparing chamber 100A, and by a transfer arm (not shown) provided in the specimen storage section 30, the specimen block is placed on the specimen block placement table 1a that exists at the position A. Thereafter, the specimen block 20 is linearly moved in a crosswise direction (±X direction shown in FIG. 1).

The specimen block placement table 1a of the specimen block transfer section 1 is configured so that the specimen block 20 can be firmly held at a placement position for the specimen block, so that even if, for example, force is applied in the −X-axial direction to the specimen block 20 when the specimen block 20 is sliced by a cutter 5a provided in the cutter section 5, as will be described later, a positional shift of the specimen block 20 from the placement position (not shown) on the specimen block placement table 1a does not occur and the accuracy of the sliced specimen 24 is not deteriorated.

In addition, the specimen block placement table 1a of the specimen block transfer section 1 can be moved to a position where a cutting surface, which is the surface layer portion after the slicing of the specimen block 20, can be sliced by the cutter 5a provided in the cutter section 5 located on the upper side of the position D, namely, to a position (referred to as a sliceable position h hereinafter) where an X-axis directional rear end of the specimen block transfer section 1 placed on the specimen block placement table 1a can reach the +X-axial direction from a blade edge of the cutter section. Also, height positions of the specimen block placement table and the cutter of the cutter section 5 (the position in the ±Z-axial direction orthogonal to the ±X-axial direction) can be relatively adjusted, so that the surface layer portion of the specimen block 20 can be sliced by the blade edge of the cutter of the cutter section.

The first charger 2 is disposed on the upper side of the specimen block transfer section 1 at the position A. By providing a positive electric charge to the surface layer portion of the specimen block 20 transferred to the position A, the surface layer portion of the specimen block 20 is positively charged.

Figure 3:
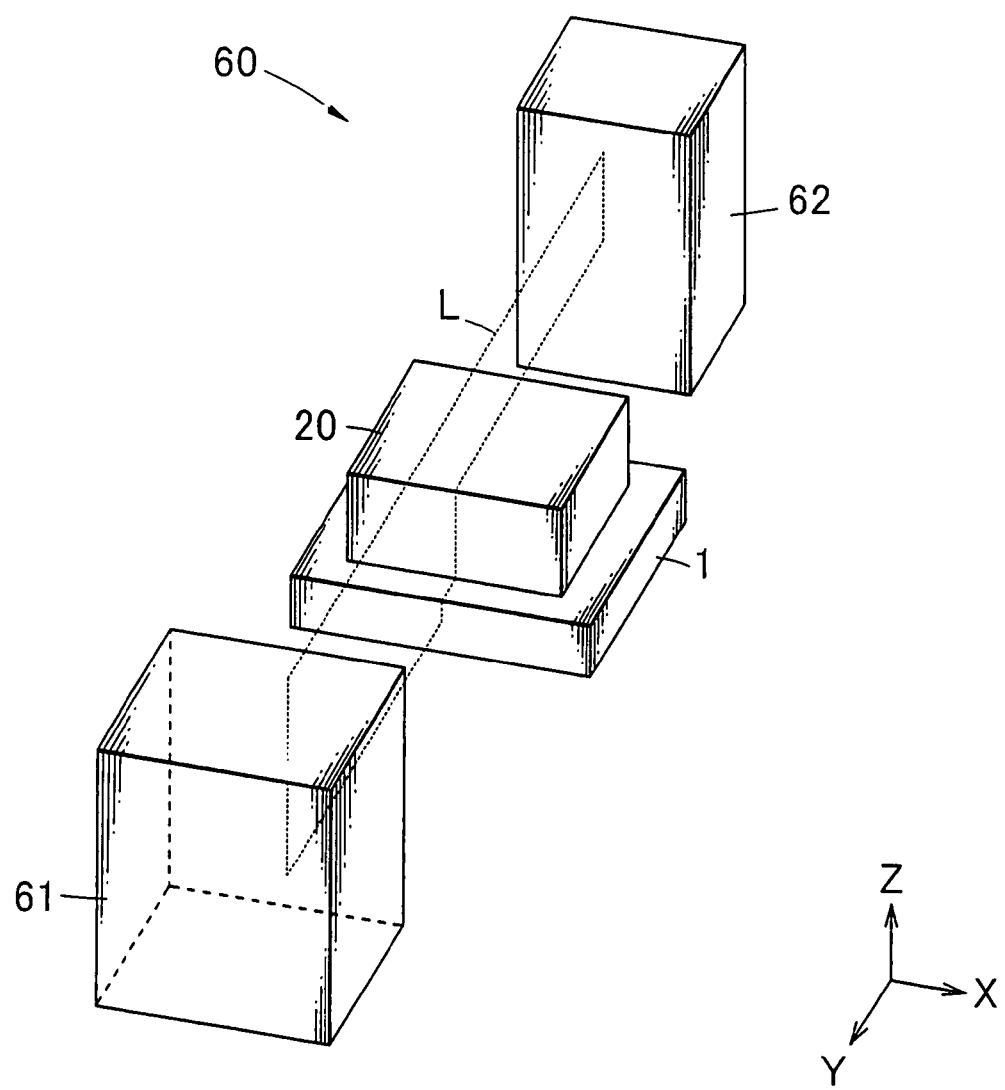
FIG. 3 is a view showing a schematic structure of a surface leveling sensor of the sliced specimen preparing apparatus of FIG. 1.

A surface leveling sensor as will be described later is provided in the vicinity of the first charger 2. The structure and the operation of this sensor will be described in detail later. As shown in FIG. 3, the surface leveling sensor 60 is a line sensor including a projector 61 and a light receiver 62. The projector 61 emits along the Y-axial direction a linear laser beam having a width of 10 mm in the Z-axial direction, and the light receiver 62 receives the light of the laser beam emitted from the projector so that an amount of the light thus received out of the emitted light can be measured. Such an amount of the light received may be obtained by directly detecting the amount of the emitted light or may be detected by the position of the light incident on a scanning line of the light receiver. It is noted that it is preferable to set the surface leveling sensor 60 at the side where the projector 61 is closer to the operator, and at the side where the light receiver 62 is farther from the operator, so as to prevent the laser beam emitted by the projector from being directed to a naked eye of the operator who operates the apparatus according to this embodiment.

The cooler 3 is disposed on the upper side of the specimen block transfer section 1 at the position B. The cooler 3 cools the specimen block 20 transferred to the position B, and a portion of the carrier tape 21 facing the specimen block 20 and supplied to the upper side of the specimen block 20 as will be described later, to a temperature lower than a temperature atmosphere in the specimen preparing chamber 100A. Advantages can be obtained by this cooling, such that the surface layer portion of the specimen block 20 can be easily sliced, and the sliced specimen 24 is easily stuck to the aforementioned portion of the carrier tape 21. It is preferable to set the cooling temperature low enough to allow condensation of the aforementioned portion of the carrier tape 21 to occur. Thus, the aforementioned advantages can be enhanced.

The second charger 4 is disposed on the upper side of the specimen block transfer section 1 at the position C. The second charger 4 provides a negative charge to the aforementioned portion of the carrier tape 21 supplied from the upper side of the position B to the upper side of the position C in synchronization with the movement of the specimen block as will be described later, to negatively charge the aforementioned portion of the carrier tape 21.

The cutter section 5 has the cutter 5*a*, and by this cutter 5*a*, an upper layer surface of the specimen block is sliced to prepare the slice. Namely, the blade edge of the cutter 5*a* is disposed to be on the XY plane located at the specimen block placement table 1*a* side (−Z axial direction side) by a thickness (e.g., 3 μm to 10 μm) of the sliced specimen 24 to be sliced, with respect to the upper end surface of the specimen block 20. Height position adjustment of the blade edge of the cutter section and the specimen block 20 is performed by changing the height of the specimen block placement table 1*a* as will be described later. The cutter section 5 functions to slice the surface layer portion of the specimen block 20 after the aforementioned height position adjustment to prepare the sliced specimen 24, when the specimen block 20 after the height position adjustment is transferred in the +X-axial direction up to the sliceable position h by the specimen block transfer section 1 with the cutter 5*a* fixed thereto. The side surface in the +X-axial direction of the specimen block 20 is, for example, preferably made vertical to the XY plane, namely parallel to the YZ plane, so as to facilitate the slicing by the cutter 5*a*.

The supply reel 6 is disposed on the upper side between the position A and the position B, together with a delivery motor (not shown). When the delivery motor is driven, the supply reel 6 can deliver the carrier tape 21 that functions as a slice auxiliary member.

The take-up reel 7 is provided in the specimen sticking chamber 100B. Constant torque is always applied to the take-up reel 7 by constant drive of the motor 71, so that the carrier tape 21 delivered from the supply reel 6 by the delivery motor can be taken up simultaneously with the delivery. The torque of the motor 71 can be changed to four stages according to the take-up diameter of the carrier tape 21 of the take-up reel 7. Driving of the delivery motor and the motor 71 to perform the delivery and take-up of the carrier tape 21 is controlled by the controller 50.

The carrier tape guide section 8 includes a plurality of guide rollers 81, 83, 91, 92, 93, and one guide bar 82. By the first and second guide rollers 81 and 83 and the guide bar 82, the carrier tape 21 is guided between the surface layer portion of the specimen block 20 transferred to the position B and the cooler 3, between the surface layer portion of the specimen block 20 transferred to the position C and the second charger 4, and in proximity to the surface layer portion of the specimen block 20 transferred to a position on the upper side of the position D and on the position D.

Figure 4:
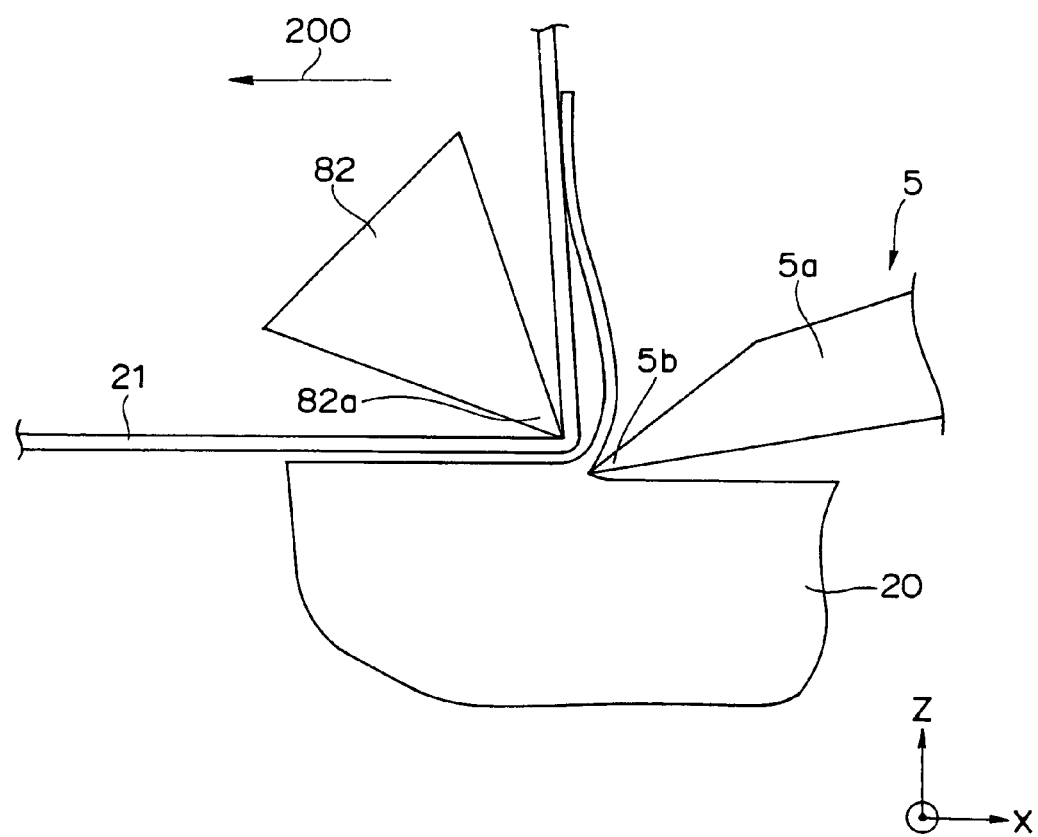
FIG. 4 is an enlarged view showing a structure in the vicinity of a guide bar of the sliced specimen preparing apparatus of FIG. 1.

The first guide roller 81 is provided between the position A and the position B of the specimen block transfer section, guides the carrier tape 21 delivered from the supply reel 6 in approximately the Z-axial direction, and turns it around in the approximately X-axial direction. In addition, as shown in FIG. 4, the guide bar 82 has a triangular cross-section, and an acute angle part 82*a* of its point end is located closely near the blade edge 5*b* of the cutter 5*a* of the cutter section 5 during slicing operation of the specimen block 20.

Figure 5:
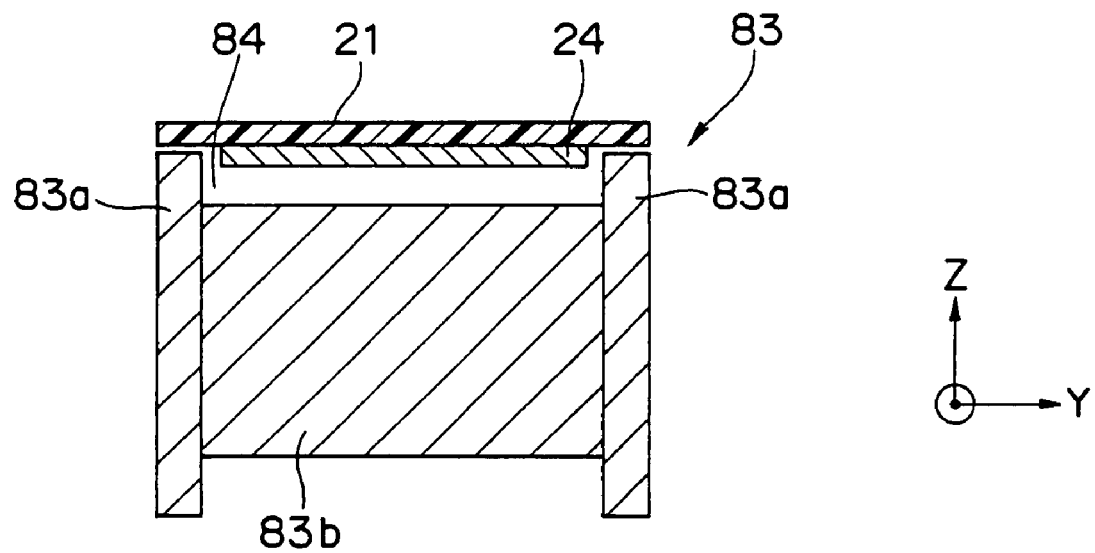
FIG. 5 is a partial enlarged view showing a structure of a second guide roller of the sliced specimen preparing apparatus of FIG. 1.

The second guide roller 83 is provided on the upper side of the guide bar 82 as shown in the figure, and guides along the approximately Z-axial direction the carrier tape guided along the X-axial direction by the guide bar 82. In addition, the second guide roller 83 is configured to have a large diameter compared to the first guide roller, and a depressed area is hardly generated in the carrier tape due to tensile force applied to the carrier tape 21 by the take-up roller 7. Moreover, as shown in FIG. 5, the second guide roller 83 has a large diameter portion 83*a* so that only both end portions of the carrier tape 21 are brought into contact therewith, and a small diameter portion 83*b* provided in an intermediate portion of the guide roller 83 and formed thinner than the large diameter portion, wherein the thin slice 24 carried by the carrier tape 21 is prevented from touching on the surface of the guide roller 83.

Note that in this embodiment, the guide bar 82 can be retreated in the −X axial direction as shown by an arrow 200, so that replacement of blades of the cutter 5*a* of the cutter section 5 and the operation such as taking-up of the carrier tape 21 can be facilitated.

Guide rollers 91 and 92 are provided so as to sandwich the thin slice 24 that exists at the position E in the specimen sticking chamber 100B, and are constituted of a pair of rollers that are fixably constituted with the carrier tape 21 between them. The guide roller 93 is configured to have the carrier tape 21 wound thereon, so that it can be guided to the take-up reel 7, at a downstream side of the position E.

Note that arrangement of the supply reel 6 and the take-up reel 7 are not limited to the above-described arrangement, and may be arranged at any places and in any numbers, provided that the carrier tape 21 can be guided by the carrier tape guide section as described above.

The slice sticking part 9 in the specimen sticking chamber 100B performs an operation of sticking the sliced specimen carried by the carrier tape 21 onto the slide, between the pair of guide rollers 91, 91 arranged on the upper side of the position E and on the upstream side (−X-axial direction side) of a traveling route of the carrier tape 21, and between the pair of guide rollers 92, 92 arranged on the upper side of the position E and on the downstream side (+X-axial direction side) of the traveling route of the carrier tape 21. For example, a portion of the carrier tape 21, to which the sliced specimen 24 is stuck, is sandwiched between the pair of guide rollers 91 and 91, and between the pair of guide rollers 92 and 92, and in this state, the pair of guide rollers 92, 92 or the pair of guide rollers 91, 91 are moved in the −Z-axial direction, thus allowing the carrier tape 21 to sag downward, and the sliced specimen 24 is brought into contact with the upper surface of the slide 22 located at the position E with the adhesive liquid 23 supplied to the upper surface as will be described later, so that the sliced specimen 24 is transferred from carrier tape 21 to the slide 22. The slide, to which the slice is transferred, is referred to as a slide with thin slice hereinafter.

As shown in FIG. 2, the slide transfer section 10 transfers one slide 22, to which the sliced specimen 24 is to be stuck next, to the position F from the slide storage section 40 that stores a plurality of slides 22, in a transfer order of the position F, position E, and position G sequentially, and places the slide 22 above a heater 61 provided in the spreading section 12 at the position G (see FIG. 2).

The adhesive liquid application section 11 is disposed on the upper side of the position F and supplies the adhesive liquid 23 onto the upper surface of the slide 22 transferred to the position F. Water or water containing ethyl alcohol and the like can be given as an example of the adhesive liquid 23. A detailed structure of the adhesive liquid application section will be described later.

The spreading section 12 includes the heater 61, and stretches wrinkles of the sliced specimen 24 by performing first heating (for example, at about 40° C. to 60° C. for several seconds to several dozen seconds) by the heater 61 on the slide 22 with the thin slice, placed on a heating plate by the slide transfer section 10, and strengthens sticking force of the sliced specimen 24 to the slide 22.

A slide return section 13 is provided in parallel to the slide transfer section 10, and carries the slide with the thin slice transferred from the slide transfer section 10 by the spreading section 12 in a direction opposite to the transfer direction of the slide transfer section 10. The slide return part 13 has a heater 62 to perform second heating (for example at about 40° C.) in addition to the first heating by using the spreading section 12, thereby completely stretching the wrinkles of the sliced specimen 24 on the slide 22, and strengthens adhesion between the sliced specimen 24 and the slide 22.

The returning transfer section 14 is a member that transfers the slide with the thin slice transferred by the slide return section 13 so as to be returned to the slide transfer section 10 again. In addition, a carrying-out section 15 is a member for carrying out the slide with the thin slice transferred by the slide return section 13 to the outside of the specimen sticking chamber 100B. Whether or not the slide with the thin slice transferred by the slide return section 13 is sent to the returning transfer section 14 or to the carrying-out section 15 is determined by the operation of a switch section 16 operated through a control signal by the controller 50. Such a structure will be described in detail later.

Next, a preparing operation of the sliced specimen 24 of the sliced specimen preparing apparatus 100 will be described. The preparing operation of this sliced specimen 24 is performed under the control of the controller 50.

First, a face preparation process of the specimen block will be described as a step of preparing the sliced specimen performed by using the sliced specimen preparing apparatus 100 according to this embodiment.

In order to prepare the sliced specimen 24 with high accuracy, the surface layer portion of the specimen block 20 having an uneven surface, being the cutting surface of the specimen block 20 after being sliced by the cutter 5a, is preferably made parallel to the flat surface (XY plane) having the sliceable position h in advance. Namely, a cutting direction of the specimen embedded in the specimen block 20 is required to be parallel to the XY plane. In order to perform such a flat face preparation, the following preparative steps are performed.

Figure 6:
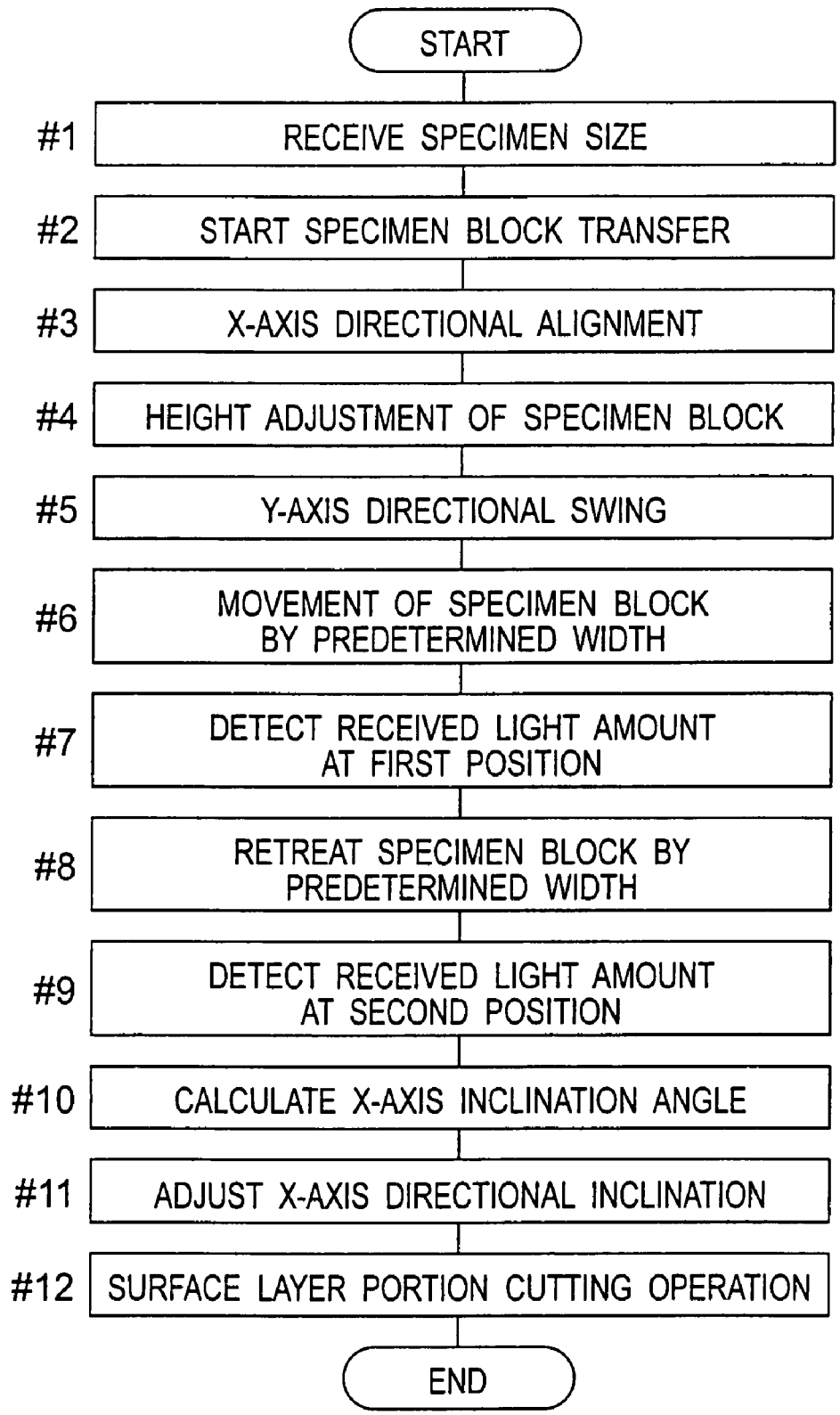
FIG. 6 is a flowchart showing a flow of processing of an initial operation.

FIG. 6 is a flowchart showing a flow of the processing of an initial operation. Such an operation is executed by operating each member as follows by the controller 50.

First, the size information of the specimen block 20 is previously inputted in the controller 50. Specifically, as the size of the specimen block 20, four sizes, i.e., 15×15×5 mm, 24×24×5 mm, 24×30×5 mm, and 24×37×5 mm are used. In the controller 50, the size used for preparing the sliced specimen is inputted and the position of the specimen block 20 in the specimen storage section 30 and the size of this block are stored (#1). Thereafter, one specimen block 20 to be subjected to the slice processing is taken out from the specimen storage section 30, which is then started to be transferred by the specimen block transfer section 1 (#2).

Subsequently, the specimen block transfer section 1 transfers the specimen block 20 along the X-axial direction, and performs alignment of the surface leveling sensor 60 in the X-axial direction of the specimen block 20 (#3). The alignment is performed so that a laser beam irradiation position of the projector 61 of the surface leveling sensor 60 is located in the vicinity of the intermediate portion of the X-axis directional dimension of the specimen block 20. Specifically, the surface leveling sensor 60 detects the amount of laser beams received by the light receiver 62 during the movement of the specimen block transfer section 1. Then, as shown in FIG. 3, when the specimen block 20 reaches the area irradiated with a laser beam L, the laser beam L is partially shielded, and as a result, the amount of light detected by the light receiver 62 is changed. In addition, as described above, the size of the specimen block 20 is previously stored in the controller, and therefore it is possible to calculate how much the specimen block 20 may be transferred from the position where the amount of light received by the light receiver is changed to align the laser beam L to the intermediate position of the specimen block 20. Namely, the controller 50 transfers the specimen block 20 so that the laser beam L is aligned to the intermediate position of the specimen block 20 after the received light amount of the laser beam by the light receiver 62 is reduced.

Figure 7:
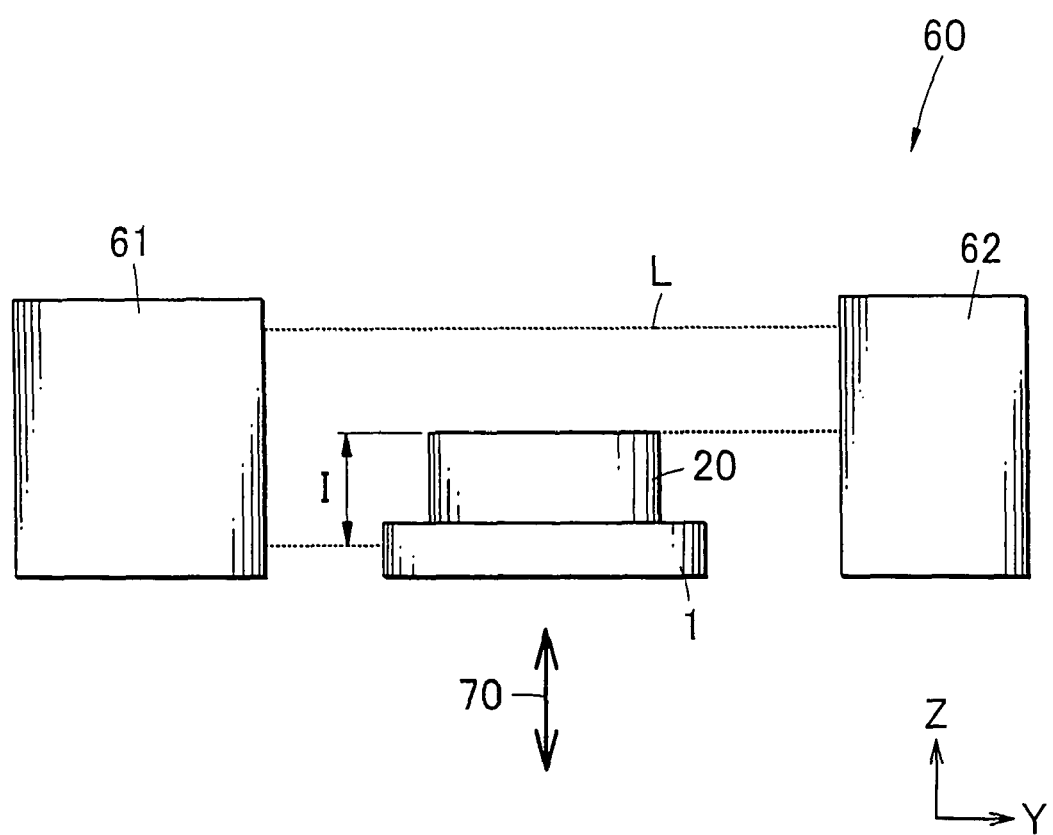
FIG. 7 is an explanatory view of a height position adjustment operation of a specimen block in the initial operation.

Subsequently, the height position adjustment of the specimen block 20 is performed (#4). As shown in an arrow 70 in FIG. 7, the height position adjustment of the specimen block is performed in such a manner that the specimen block 20 (the height of the specimen block transfer section 1 is adjusted as the operation of the controller 50) is moved in the Z-axial direction, and an amount I, being the amount of the laser beam L shielded by the specimen block 20 is made constant. In this embodiment, specifically, the shielded amount I of the laser beam L by the specimen block 20 is set to 7 mm. It is noted that the value of the shielded amount is not limited to 7 mm, and for example, an appropriate value can be selected according to a thickness dimension of the specimen block and a distance between the projector 61 and the specimen block 20. By making the shielded amount constant, the initial value of detection by the light receiver 60 can be made constant, thus making it possible to facilitate received light amount control as described below. In addition, when the shielded amount is small, the laser beam L is reflected by the surface of the specimen block and the received light amount is hardly stabilized. Accordingly, the shielded amount is taken large (7 mm to 9 mm), thereby preventing reflected light from being received. Even when the shielded amount is small, the reflected light can be prevented from being received, by keeping the light receiver away from the specimen block.

Figure 8:
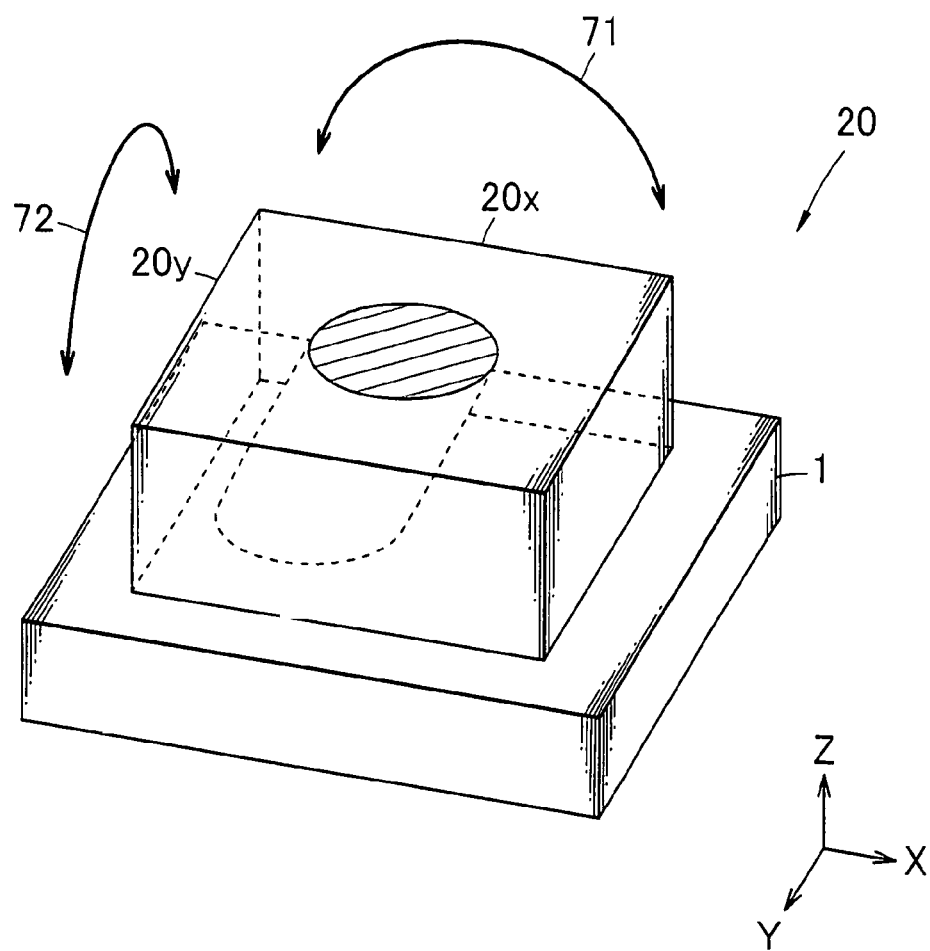
FIG. 8 is an explanatory view in a swing direction of the specimen block in the initial operation.

Next, the controller 50 performs swing processing of detecting the change in the received light amount of the surface leveling sensor 60 while performing a swing operation of the specimen block transfer section 1. As shown in FIG. 8, the swing direction of the specimen block 20 in which the specimen block transfer section 1 can be operated is shown by two directions, i.e., the X-axial direction 71 and the Y-axial direction 72. These swing directions are defined as follows. Namely, the X-axial direction 71 is a direction of swinging the specimen block 20 so as to change the inclination of a side 20x extending in a direction along the X-axis, and the Y-axial direction 72 is a direction of swinging the specimen block 20 so as to change the inclination of a side 20y extending in a direction along the Y-axis.

At this time, the surface leveling sensor 60 detects the change in the received light amount by the light receiver 62 during the swing operation of the specimen block 20 in the Y-axial direction. Namely, when the top face of the specimen block 20 is inclined with respect to the laser beam L, an area of shielding the laser beam by the specimen block 20 is increased. Accordingly, by making the shielded amount of the laser beam the smallest, a swing amount of the specimen block in the Y-axial direction can be calculated, thus making it possible to perform flat face preparation in the Y-axial direction. When the shielded amount of the laser beam is the smallest, namely, when the received light amount by the light receiver is the largest, this means that an irradiation direction of the laser beam and the top face of the specimen block are parallel to each other. As described above, the laser beam is emitted in the Y-axial direction, and therefore by detecting this value, the swing angle of the specimen block 20 in the Y-axial direction can be made parallel to the Y-axis.

Figure 9:
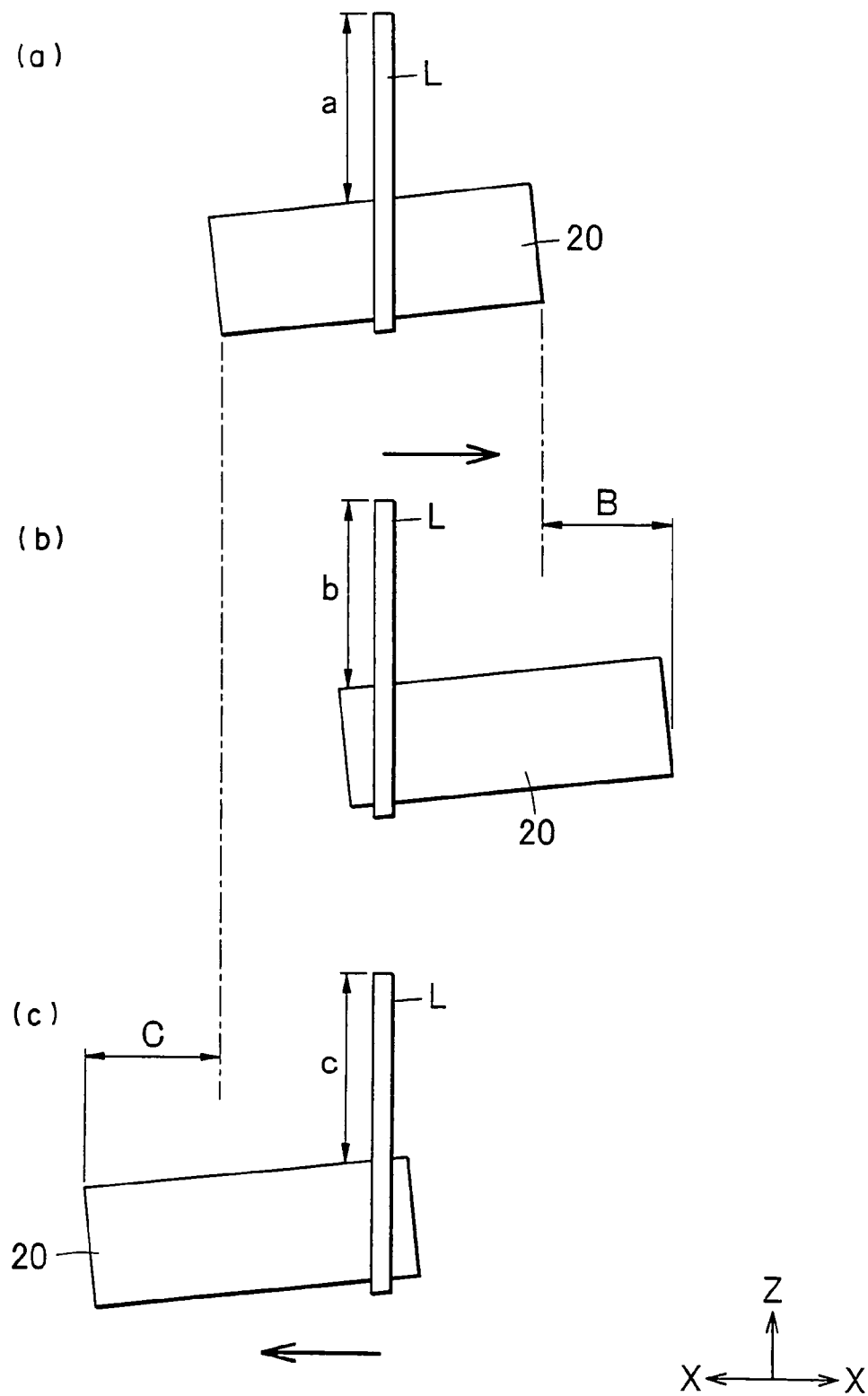
FIG. 9 is a view illustrating an operation of detecting a swing angle in an X-axial direction.

Next, the operation of detecting the swing angle in the X-axial direction is performed. FIG. 9 illustrates the operation of detecting the swing angle in the X-axial direction. In this processing, each process as described below is continuously performed. First, the specimen block transfer section 1 is driven from a state shown in FIG. 9(a), and the specimen block is moved in the X-axial direction by a predetermined width B (#6). FIG. 9(b) shows a state where the specimen block is moved by the predetermined width B. This predetermined width B is determined by the size of the specimen block 20. Specifically, this predetermined width B is set to 5.0 mm in the specimen block with the size of 15×15×5 mm, 8.5 mm in the specimen block with the size of 24×24×5 mm, 10.0 mm in the specimen block with the size of 24×30×5 mm, and 16.0 mm in the specimen block with the size of 24×37×5 mm. Namely, in order to calculate the swing angle in the X-axial direction, this predetermined width B is set as longer as possible for the specimen block, and is set to be a distance capable of being surely detected by the surface leveling sensor 60.

In a state shown in FIG. 9(b), a received light amount "b" of the light receiver 62 is detected with the position obtained by moving the specimen block by the predetermined width B set as a first position (#7). When the specimen block 20 is in a state of being inclined in the X-axial direction, it is found that the received light amount "b", with the specimen block moved by the predetermined width B, is changed from the received light amount "a" in the initial state.

Next, as shown in FIG. 9(c), the specimen block is moved from the initial state shown in FIG. 9(a) in the X-axial direction by a predetermined width C. Namely, the specimen block transfer section 1 is moved in the −X-axial direction by the width of B+C (#8). Here, the predetermined width C may be the same as the width B or may be a different width from the width B. In this embodiment, the predetermined width C is set as the same width as the width B.

Next, in a state shown in FIG. 9(c), a received light amount "c" of the light receiver 62 is detected with the specimen block moved by the predetermined width C set as a second position (#9).

Figure 10:
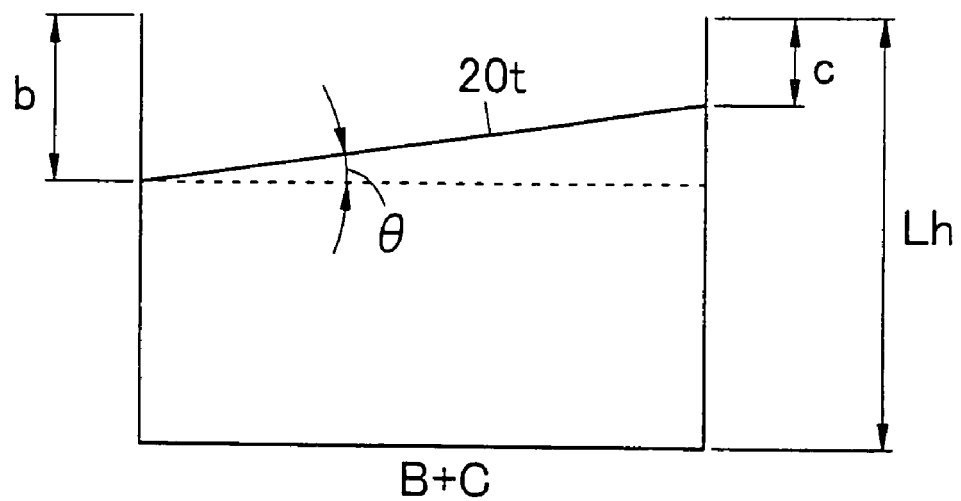
FIG. 10 is an explanatory view showing a principle of calculation of an inclination angle.

The inclination angle of the specimen block 20 in the X-axial direction is calculated from the received light amount "b" at the first position and the received light amount "c" at the second position obtained as described above (#10). FIG. 10 illustrates a principle in calculating the inclination angle. As described above, by detecting the received light amount "b" at the first position and the received light amount "c" at the second position, the height at each position can be calculated in the vicinity of the specimen block 20. Namely, since a width Lh in the Z-axial direction of the laser beam L is already known, the height of the top face 20t of the specimen block 20 can be detected by calculating the received light amount "b" or "c". In addition, since the specimen block is moved by the predetermined widths B and C, the interval between the first position and the second position can be calculated as a sum of B+C. Accordingly, an inclination angle θ to a surface parallel to the top face 20t can be calculated.

The specimen block transfer section 1 performs inclination adjustment of the swing angle in the X-axial direction, by the inclination angle θ in the X-axial direction thus calculated (#11). This swing adjustment may be performed so that the top face 20t of the specimen block 20 is horizontal, or may be performed to have a predetermined angle. Namely, such an angle of slice is defined in some of the specimens embedded in the specimen block 20, and in some cases, the thin slice is required to be prepared so as to be adjusted to this angle. When this operation is completed, the inclination angle of the specimen block in the X-axial direction is fixed as a predetermined value, and a cutting operation of the surface layer portion as will be described below is performed (#12).

In the cutting operation of the surface layer portion, the specimen block 20 is transferred by the specimen block transfer section 1, so as to pass through the position A, the position B, and the position C, and is transferred to the sliceable position "h" (see FIG. 1) on the position D, with the height position (position in the ±Z-axial direction) of the specimen block 20 adjusted so that the surface layer portion of the specimen block 20 is located on the XY plane including the sliceable position "h" during the transfer.

By the movement of the specimen block 20 to the sliceable position "h", the surface layer portion of the specimen block 20 is sliced by the cutter 5a of the cutter section 5 fixed at a slicing preparation position H, and the cutting surface parallel to the flat surface (XY plane) including the sliceable position "h" is formed in the specimen block 20. Namely, as described above, after the inclination angle in the X-axial direction is determined to be a predetermined value, the surface layer portion of the top face 20*t* of the specimen block 20 is cut off by the cutter section 5*a* (#12). The face preparation process of the specimen block is performed as described above, and the preparation for slicing as shown below is completed.

Next, preparing operation of the sliced specimen 24 after the completion of the initial operation will be described. First, the specimen block 20 with its height position adjusted, is transferred to the sliceable position "h" on the position D from the position A, so that the cutting surface is located on the XY plane including the sliceable position "h".

At this time, when the specimen block 20 after the height position adjustment passes through the position A, positive charge is supplied by the first charger 2 to the cutting surface of the specimen block 20 after the height position adjustment, to positively charge the cutting surface of the specimen block 20.

In addition, when the specimen block 20 after the height position adjustment passes over the position B, the cutting surface of the specimen block 20 after the height position adjustment and a portion (a slice holding portion) of the carrier tape 21 located on the upper side of the position B and facing the specimen block 20 after the height position adjustment are cooled by the cooler 3.

Subsequently, when the specimen block 20 after the height position adjustment is moved to the position C from the position B, the delivery motor (not shown) is driven so that the slice holding portion of the carrier tape 21 is moved while the facing state with the specimen block 20 after the height position adjustment is maintained, in synchronization with the movement of the specimen block 20 after the height position adjustment.

Subsequently, when the specimen block 20 after the height position adjustment passes over the position C, negative charge is supplied by the second charger 4 to the slice holding portion of the carrier tape 21 that moves to the upper side of the position C in synchronization with the movement of the specimen block 20 after the height adjustment. Thus, the slice holding portion of the carrier tape 21 is negatively charged.

Subsequently, when the specimen block 20 after the height position adjustment is transferred to the sliceable position "h" on the position D from the position C by the specimen block transfer section 1, the surface layer portion of the specimen block 20 after the height adjustment contacts the cutter 5*a* of the cutter section 5 fixed at the slicing preparation position H, which is then sliced when the specimen block transfer section 1 is transferred, to thereby prepare one sheet of the sliced specimen 24. In addition, at this time, the carrier tape 21 travels in synchronization with the transfer speed of the specimen block transfer section 1, and the sliced specimen sliced by the cutter 5*a* is stuck to the carrier tape 21 and is carried thereby.

When the cutting surface of the specimen block 20 after the height position adjustment is sliced by the cutter 5*a* of the cutter section 5, the specimen block 20 after the height position adjustment is stopped at the sliceable position "h" when transferred to this sliceable position "h" on the position D. Meanwhile, the slice holding portion of the carrier tape 21 that moves in synchronization with the movement of the specimen block 20 after the height position adjustment leaves the specimen preparing chamber 100A and continues to move up to the specimen sticking chamber 100B.

Note that when the carrier tape 21 moves to the specimen sticking chamber 100B, the sliced specimen 24 is charged positively as described above, and the portion of the carrier tape 21 facing the sliced specimen 24 is charged negatively. Therefore, the sliced specimen 24 is in a state of being stuck to the portion of the carrier tape by static charge and a cooling effect by the cooler 3.

The sliced specimen 24 sent to the specimen sticking chamber 100B is stuck to the slide as will be described later, to thereby prepare the slide with the thin slice. In the sliced specimen preparing apparatus according to this embodiment, a plurality of sliced specimens 24 can be stuck to one sheet of the slide. This operation will also be described in detail later.

In the above-described structure, when the sliced specimen 24 is moved to the upper side of the position E, the specimen block 20 that is stopped at the sliceable position "h" on the position D is returned to the position A from the position D by the specimen block transfer section 1 to prepare the next sliced specimen 24, and the height position of the specimen block 20 (the position in the ±Z-axial direction) is adjusted so that the cutting surface of the specimen block 20 after the first one sheet of sliced specimen 24 is prepared is located on the XY plane including the sliceable position "h".

In the same way as described above, the specimen block 20 is transferred to the position D from the position A by the specimen block transfer section 1, the slicing operation is automatically and continuously repeated for an arbitrary number of times, to thereby prepare an arbitrary number of sheets of sliced specimens 24.

Next, the structure and the operation of the cutter section 5 will be described in detail.

Figure 11:
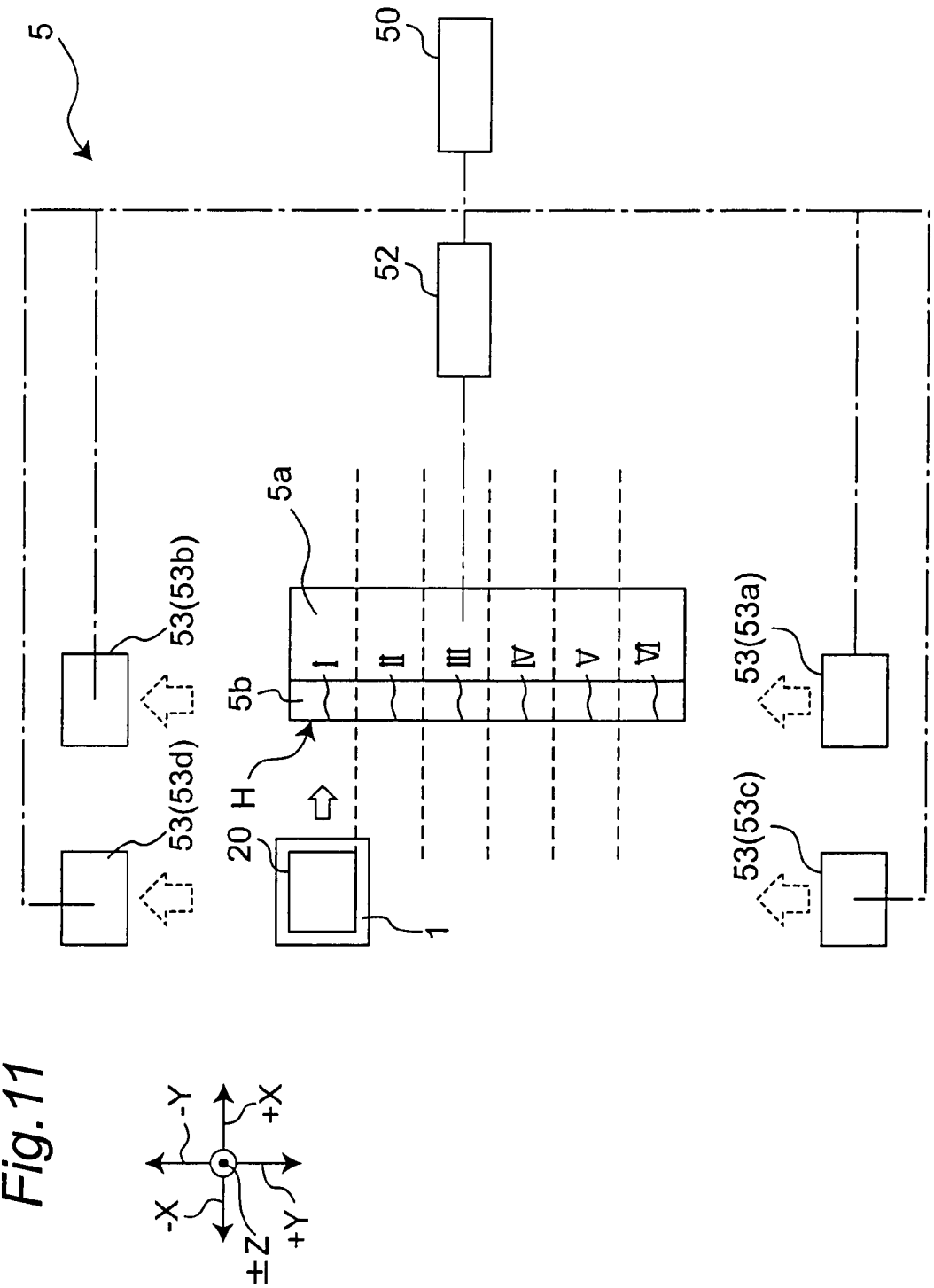
FIG. 11 is a front view showing a schematic structure of a cutter section provided in the sliced specimen preparing apparatus according to the embodiment of the present invention.
Figure 12:
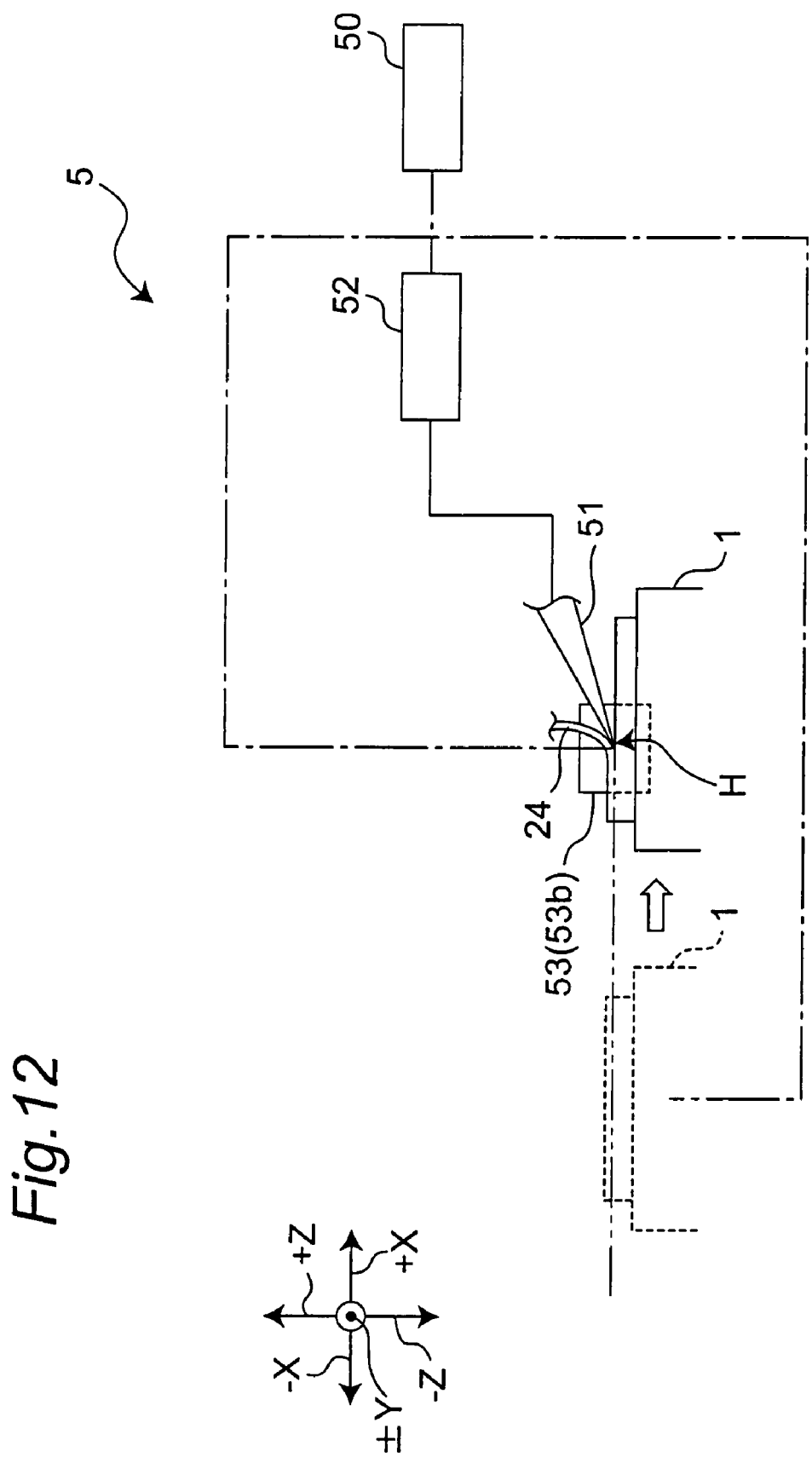
FIG. 12 is a side view showing the schematic structure of the cutter section provided in the sliced specimen preparing apparatus according to the embodiment of the present invention.

FIG. 11 is a plan view showing a schematic structure of the cutter section 5. FIG. 12 is a side view showing the schematic structure of the cutter section 5.

In FIGS. 11 and 12, the cutter section 5 has the cutter 5*a*, a blade edge contacting position changing part 52, and a detector 53.

The cutter 5*a* has a length in a width direction (also referred to as an extending direction of the blade) sufficiently larger than the length in a width direction (the ±Y-axial direction orthogonal to the ±X-axial direction and the ±Z-axial direction) of the specimen block 20. The cutter 5*a* is disposed so that any one of contacting areas I to VI (see FIG. 11) of the blade edge 5*b* extending in the width direction (±Y-axial direction) can firstly contact the specimen block 20. Each of the contacting areas I to VI of the blade edge 5*b* of the cutter 5*a* has a length in the width direction, longer than the length of the specimen block 20 in the width direction, so as to be capable of performing slicing without allowing the specimen block 20 transferred to the sliceable position "h" (see FIG. 1) to contact other contacting areas. In FIG. 11, the blade edge 5*b* of the cutter 5*a* is disposed so as to be orthogonal (so as to extend in the ±Y-axial direction) to a transfer direction (±X-axial direction) of the specimen block 20. However, the blade edge 5*b* may be inclined at a predetermined angle.

The blade edge contacting position changing part 52 is configured so that the cutter 5*a* can be moved in a direction (±Y-axial direction and the extending direction of the blade) orthogonal to the transfer direction (±X-axial direction) of the specimen block 20, to sequentially change the position where the blade edge 5*b* of the cutter 5*a* firstly contacts the specimen block 20, namely, change this position to the contacting areas I to VI.

The detector 53 includes a projector 53*a* that projects light, and a light receiver 53*b* that receives the light projected by the projector 53*a*, and the projector 53*a* and the light receiver 53*b* are disposed to face each other with the cutter 5*a* sandwiched between them in the ±Y-axial direction (for example, in the vicinity of the slicing preparation position H). The detector 53 is capable of measuring the height (±Z-axial direction) position of the blade edge 5b of the cutter 5a, based on the difference between the light amount of the light projected from the projector 53a and the light amount received by the light receiver 53b.

In addition, the detector 53 includes a projector 53c that projects light, and a light receiver 53d that receives the light projected by the projector 53c, and the projector 53c and the light receiver 53d are disposed to face each other with the transfer route of the specimen block 20 positioned between them in the ±Y-axial direction on the upstream side (for example, in the vicinity of the position A) of the transfer direction (±X-axial direction) of the specimen block 20. The detector 53 is capable of measuring the height (±Z-axial direction) position of the cutting surface of the specimen block 20 transferred to the sliceable position "h", based on the difference between the light amount of the light projected from the projector 53c and the light amount received by the light receiver 53d.

The operations of the blade edge contacting position changing part 52 and the detector 53 are controlled by the controller 50.

Figure 14:
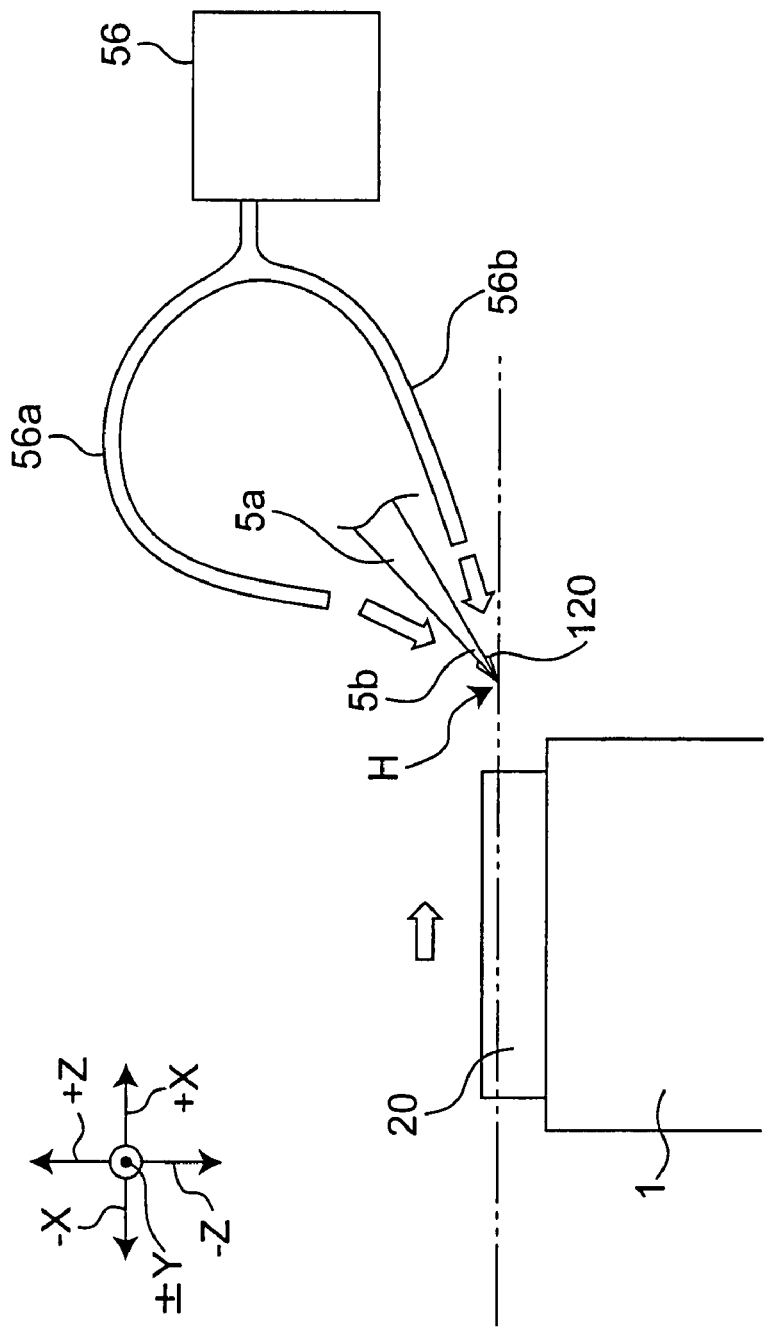
FIG. 14 is a side view showing a constitutional example of an air supply section of the cutter section provided in the sliced specimen preparing apparatus according to the embodiment of the present invention.

In addition, as shown in FIG. 14, the cutter section 5 includes nozzles 56a and 56b discharging compressed air (shown by an arrow) toward the blade edge 5b of the cutter 5a, and an air supply section 56 that supplies the compressed air to the nozzles 56a and 56b. When the blade edge 5b of the cutter 5a does not contact the specimen block 20, the compressed air is blown from two directions of the +Z-axial direction side and the −Z-axial direction side of the blade edge 5b of the cutter 5a, to thereby blow off an adhering substance 120 such as paraffin adhering to the blade edge 5b of the cutter 5a by the slicing operation. With this structure, the deterioration of the cutting quality in one contacting area of the blade edge 5b of the cutter 5a can be reduced, and the number of times of replacement of the cutter 5a can be further reduced than in conventional apparatuses. Therefore, the burden of the operator can be reduced, while maintaining the accuracy required for the sliced specimen 24.

Figure 13:
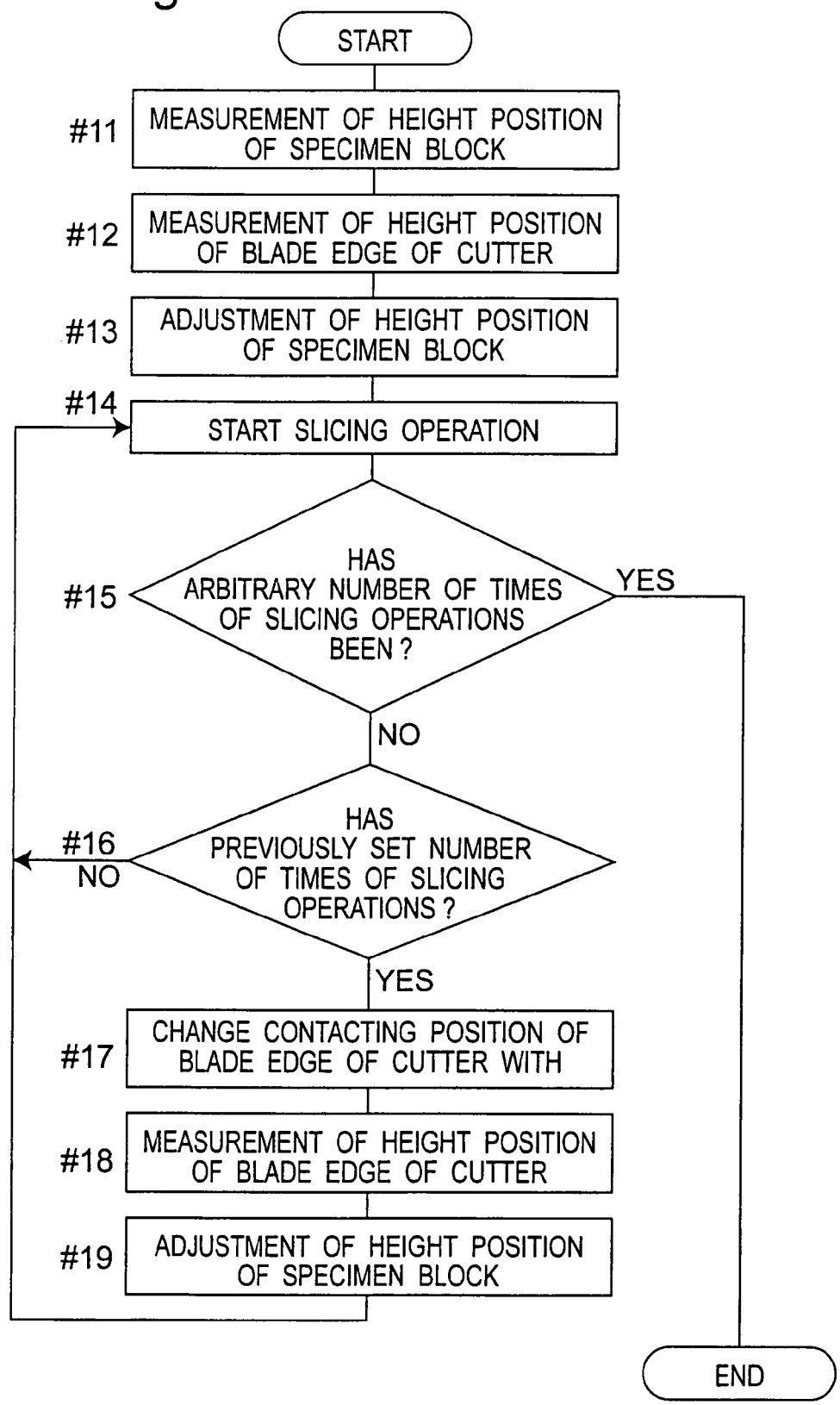
FIG. 13 is a flowchart showing the steps of preparing a plurality of sliced specimens in the sliced specimen preparing apparatus according to the embodiment of the present invention.

Next, the operation of the cutter section 5 for preparing a plurality of sliced specimens 24 will be described. Part overlapped with the description of the slicing operation will be omitted in the description below. FIG. 13 is a flowchart showing the operation of the cutter section 5. The operations of the blade edge contacting position changing part 52 of the cutter section 5 and the detector 53 are performed under the control of the controller 50.

Here, the description is given on the assumption that the initial operation and the like is performed, and the cutting surface parallel to the XY plane is formed on the surface layer portion of the specimen block 20, and the specimen block 20 is disposed between the projector 53c and the light receiver 53d of the detector 53 by the specimen block transfer section 1.

First, the detector 53 measures the height (±Z-axial direction) position of the cutting surface of the specimen block 20, by projecting light from the projector 53c and receiving the light projected from the projector 53c by the light receiver 53d with the specimen block 20 disposed between the projector 53c and the light receiver 53d (#11).

Subsequently to the operation of the above-described #11, or simultaneously with the operation of the above-described #11, the detector 53 measures the height (±Z-axial direction) position of the blade edge 5b of the cutter 5a, by projecting light from the projector 53a to the blade edge 5b of the cutter 5a disposed at the slicing preparation position H between the projector 53a and the light receiver 53b, and receiving the light thus projected from the projector 53a by the light receiver 53b (#12).

Subsequently, based on the measurement information of the cutting surface of the specimen block 20 and the height position of the cutter 5a measured by the detector 53, the specimen block 20 is moved in the ±Z-axial direction by the specimen block transfer section 1, so that the height position of the cutting surface of the specimen block 20 is located on the plane (namely, the plane including the sliceable position "h") set apart from the height position (namely, the slicing preparation position H) of the blade edge 5b of the cutter 5a to the +Z-axial direction side by the thickness of the sliced specimen 24, to thereby adjust the height position of the specimen block 20 (#13).

Subsequently, the specimen block 20 after the adjustment of the height position is transferred to the sliceable position "h" on the position D from the position A, with the blade edge 5b of the cutter 5a fixed to the slicing preparation position H, and the surface layer portion of the specimen block 20 is sliced in any one of the contacting areas (for example, contacting area I) of the blade edge 5b of the cutter 5a. Namely, the slicing operation is started (#14).

Subsequently, every time one slicing operation is completed, the controller 50 determines whether or not the slicing operation of arbitrary numbers of times (such as 100 numbers of times) in the aforementioned contacting area of the blade edge 5b of the cutter 5a has been completed (#15). The aforementioned arbitrary numbers of times are set according to the number of sliced specimens 24 and the kind of the sliced specimen 24 required by the operator, before the slicing operation is started automatically and continuously using the sliced specimen preparing apparatus 100 by the operator.

In the above-describe #15, when the controller 50 so determines that the slicing operation of the arbitrary number of times has been completed, the slicing operation is stopped. Meanwhile, when the controller 50 so determines that the slicing operation of the arbitrary number of times has not been completed, the controller 50 then determines whether or not the slicing operation of previously set number of times (such as number of times) has been completed (#16). The aforementioned previously set number of times is suitably set according to a material quality and the like by the operator, before the slicing operation is started automatically and continuously using the sliced specimen preparing apparatus 100 by the operator, and is preferably set to the number of times in a range where the cutting quality of the blade edge 5b of the cutter 5a is not deteriorated by the automatic and continuous slicing operation.

In the above-described #16, when the controller 50 so determines that the slicing operation of previously set number of times has not been completed, the process returns to the #14 to repeat the slicing operation. Meanwhile, when the controller 50 so determines that the slicing operation of the previously set number of times has been completed, the blade edge contacting position changing part 52 moves the cutter 5a in the ±Y-axial direction (extending direction of the blade) so that the position where the blade edge 5b of the cutter 5a firstly contacts the specimen block 20 is changed to a contacting area different from the aforementioned contacting area (e.g., contacting area II) (#17). At this time, as described above, a shift occurs in some cases in the height position of the blade edge 5b of the cutter 5a, before and after the movement depending on an individual variability of the cutter 5a. Namely, in this case, the slicing preparation position H is shifted in the ±Z-axial direction.

Therefore, the detector 53 measures the height (±Z-axial direction) position of the blade edge 5b of the cutter 5a after the movement (after the change), by projecting light from the projector 53a and receiving the light thus projected from the projector 53a by the light receiver 53b, in the state where the cutter 5a is disposed between the projector 53a and the light receiver 53b (#18).

Subsequently, based on the measurement information of the height position of the blade edge 5b of the cutter 5a after the movement measured by the detector 53, the specimen block 20 is moved in the ±Z-axial direction by the specimen block transfer section 1 so that the height position of the cutting surface of the specimen block 20 is located on the plane set apart from the height position of the blade edge 5b of the cutter 5a after the movement to the ±Z-axial direction side by the thickness of the sliced specimen 24, to thereby adjust the height position of the specimen block 20 (#19). In other words, the sliceable position "h" in the ±Z-axial direction is corrected according to the shift of the slicing preparation position H in the ±Z-axial direction. Thus, the distance between the specimen block 20 and the blade edge 5b of the cutter 5a of the cutter 5a after the movement in the ±Z-axial direction is maintained at the distance of the thickness of the sliced specimen 24. Thereafter, the process returns to the above-described #14, and the slicing operation is resumed.

As described above, by moving the cutter section 5 and changing operation of the contacting area of slicing the specimen block, a plurality of sliced specimens 24 can be prepared by one cutter 5a.

It is noted that as described above, the cutter 5a is fixed at the slicing preparation position H and the specimen block 20 is moved to the sliceable position "h" to thereby slice the surface layer portion of the specimen block 20. However, the present invention is not limited to this structure. For example, the sliced specimen preparing apparatus 100 may be configured to perform the slicing operation by moving the cutter 5a in the ±X-axial direction on the XY plane with the specimen block 20 fixed at the sliceable position "h". Namely, the sliced specimen preparing apparatus 100 may be configured so that the slicing operation is performed by relatively moving the specimen block 20 and the cutter 5a. As an example of moving the cutter 5a, a cutter horizontal movement section (not shown) that moves the cutter 5a in the ±X-axial direction is provided separately, and the cutter 5a is moved in the −X-axial direction by the cutter horizontal movement section to slice the specimen block 20 with the specimen block 20 transferred to the sliceable position "h" by the specimen block transfer section 1 and stopped (fixed), to thereby prepare the sliced specimen 24.

In addition, the adjustment operation of the height position of the specimen block 20 and the cutter 5a is not limited to the above-described operation, and may be performed until the specimen block 20 is transferred from the position D to the position A by the specimen block transfer section 1 and is transferred to the position D from the position A again.

In addition, as described above, by moving the specimen block 20 in the ±Z-axial direction (height direction), the adjustment of the height position for slicing is performed. However, the present invention is not limited thereto. For example, the adjustment of the height position for slicing may be performed by moving the cutter 5a in the ±Z-axial direction (thickness direction of the blade).

Next, the structure and the operation of each member provided in the specimen sticking chamber 100B will be described in detail. It is noted that in the description given hereunder, when the slide is moved by each member, the description will be given with a branch number assigned to each member such as slides 22-1, 22-2, or operation pieces 52-1, to discriminate the position where the slide or the aforementioned each member exists. However, these branch numbers do not denote different members.

As shown in FIG. 2, the slide storage section 40, the slice sticking part 9, the slide transfer section 10, the adhesive liquid application section 11, the spreading section 12, the slide return section 13, the returning transfer section 14, the carrying-out section 15, the switch section 16, and the take-up reel 7 are provided in the specimen sticking chamber 100B.

The slide storage section 40 stores an unused slide to which a thin slice is stuck, and supplies the slide 22 to the slide transfer section 10 under the control of the controller 50.

The slide transfer section 10 transfers the slide along the Y-axial direction. The slide transfer section 10 includes a guide section 31 that holds a portion near both longitudinal ends of the slide 22-1 transferred from the slide storage section 40, a guide bar 32 provided parallel to the guide section, and a movement section 33 that moves along the guide bar 32 by pushing out the slide. The movement section 33 is movably held along the guide bar 32 through the guide bar 32, and is moved along the guide bar 32 when a drive belt 34 is driven. The drive belt 34 is wound on rollers 35a and 35b provided near the both ends of the guide bar 32. The roller 35a is rotary-driven by a motor 36, and by rotary-driving the roller 35a, the drive belt 34 is driven, to move the movement section 33. The movement section 33 abuts on a transfer-directional rear end of the slide placed on the guide section 31, to move the slide to the position G through the position F and the position E by the movement of the movement section 33.

Figure 15A:
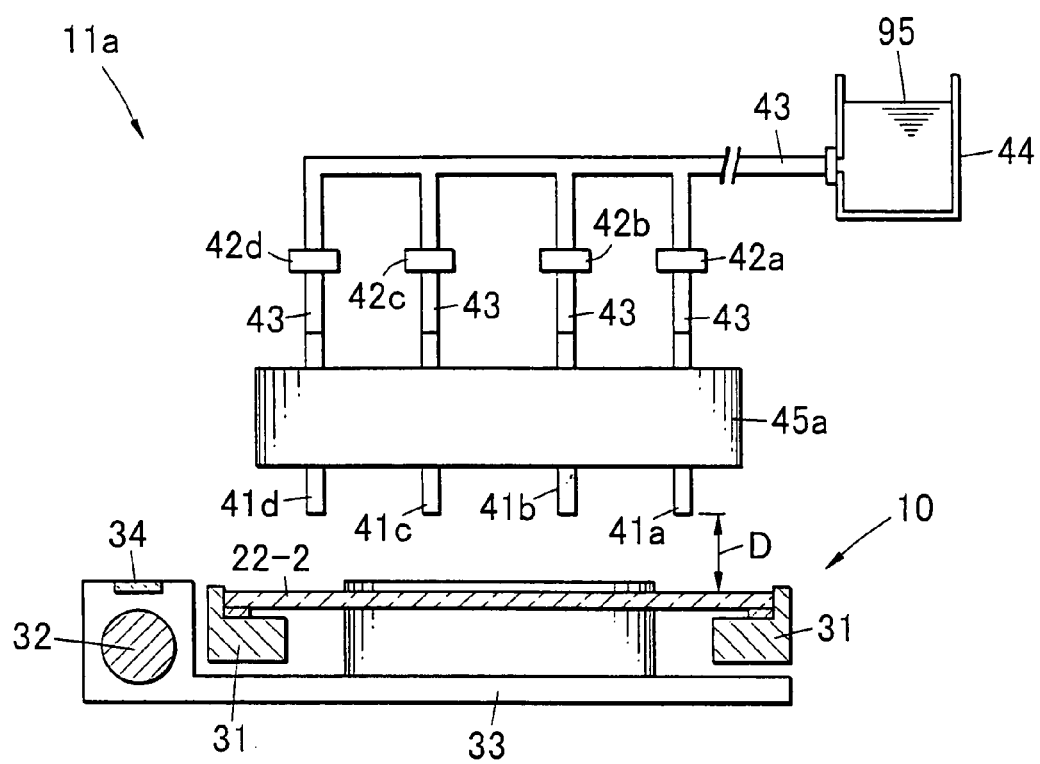
FIG. 15A is a schematic view showing another constitutional example of an adhesive liquid application section used in the sliced specimen preparing apparatus shown in FIG. 1.
Figure 15B:
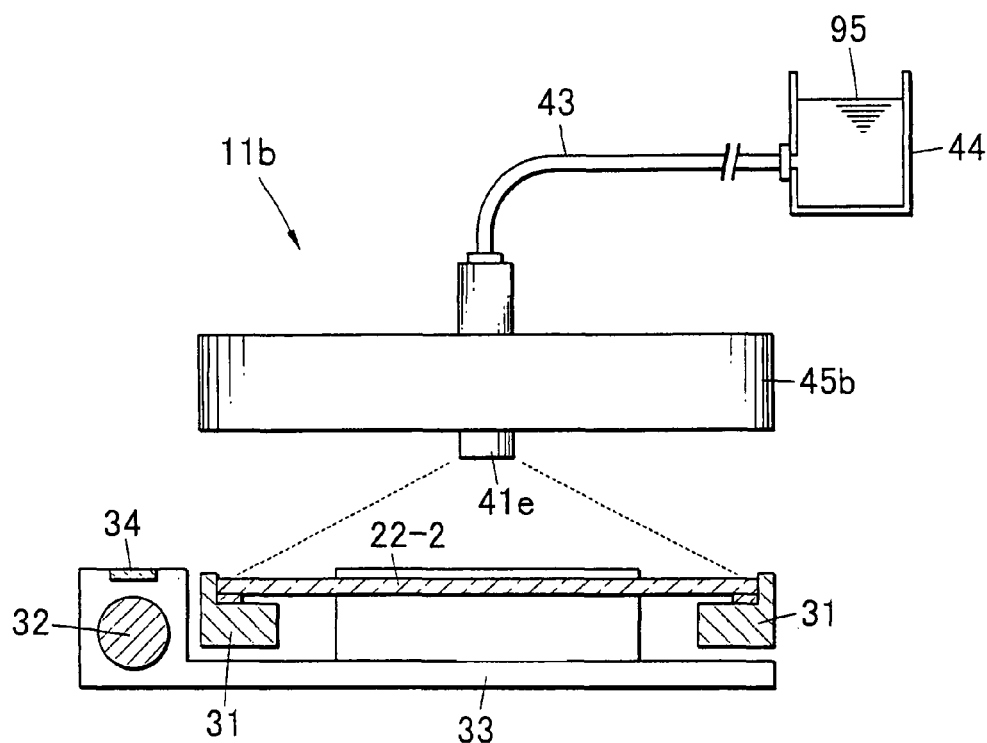
FIG. 15B is a schematic view showing another constitutional example of the adhesive liquid application section used in the sliced specimen preparing apparatus shown in FIG. 1.

The adhesive liquid application section 11 is provided in the middle of the guide section 31 of the slide transfer section 10. The adhesive liquid application section 11 functions to apply the adhesive liquid on the slide 22-2 transferred by the slide transfer section 10, and for example, the adhesive liquid application sections shown in FIGS. 15A and 15B are given as specific structures. FIG. 15A is a schematic view showing a constitutional example of the adhesive liquid application section used in the sliced specimen preparing apparatus shown in FIG. 1. FIG. 15B is a schematic view showing another constitutional example of the adhesive liquid application section used in the sliced specimen preparing apparatus shown in FIG. 1.

An adhesive liquid application section 11a shown in FIG. 15A includes a nozzle unit 45a having a plurality of nozzles (four in this embodiment) for applying the adhesive liquid onto the surface of the slide 22-2. Each nozzle provided in the nozzle unit 45a is arrayed side by side in a longitudinal direction (X-axial direction) of the slide, so that the nozzle that discharges the adhesive liquid can be suitably selected according to an application position of the slide. Each of the nozzles 41a, 41b, 41c, and 41d is communicated with an adhesive liquid tank 44, in which an adhesive liquid 95 is stored, by a supply tube 43. The adhesive liquid tank 44 is provided at a position higher than the nozzles 41a, 41b, 41c, and 41d, so that the adhesive liquid is supplied to the nozzles 41a, 41b, 41c, 41d by gravitational force and is discharged. With consumption of the adhesive liquid in the adhesive liquid tank 44, the distance between a liquid face of the adhesive liquid tank 44 and a nozzle tip is changed. Therefore, with the consumption of the adhesive liquid, the height directional position of the adhesive liquid tank may be adjustably constituted. By thus supplying the adhesive liquid by gravitational force, a pump for supplying and discharging the adhesive liquid is not required to be provided. Opening/closing valves 42a, 42b, 42c, and 42d are provided in the middle of the supply tube 43 for every nozzle, and under the control of the controller 50, timing of opening/closing is controlled so that any quantity of the adhesive liquid can be discharged from any nozzle. The opening/closing valves 42*a*, 42*b*, 42*c*, and 42*d* are preferably provided in the vicinity of the nozzles 41*a*, 41*b*, 41*c*, and 41*d*.

The nozzles 41*a*, 41*b*, 41*c*, and 41*d* are arranged with a predetermined distance D from the surface of the slide 22, so that droplets are diffused by impact produced when the adhesive liquid dropped from the nozzle impinges on the surface of the slide. In addition, the nozzle unit 45*a* may be configured such that the distance D is set adjustable and by adjusting this distance, the diffusion of the adhesive liquid dropped from the nozzle can be adjusted.

An adhesive liquid application section 11*b* shown in FIG. 15B includes a nozzle unit 45*b* having a single nozzle 41*e* for applying the adhesive liquid onto the surface of the slide 22-2. The nozzle 41*e* provided in the nozzle unit 45*b* is arranged in a longitudinal central portion of the slide, so that misty adhesive liquid can be discharged at wide angles. The nozzle 41*e* is communicated with the adhesive liquid tank 44, in which the adhesive liquid 95 is stored, by the supply tube 43. The adhesive liquid application section 11*b* thus configured includes a pump (not shown) for discharging the adhesive liquid from the nozzle, and a drive timing of the pump is controlled by the controller 50. According to the adhesive liquid application section 11*b* with this configuration, by the discharge of the misty adhesive liquid from the nozzle 41*e*, the adhesive liquid can be applied extremely thinly over a wide range. Accordingly, irrespective of a tight adhering position of the thin slice to the slide as will be described later, the adhesive liquid can be applied onto the slide by the same control processing, thus making it possible to facilitate the control.

The slice sticking part 9 is provided on the downstream side of the adhesive liquid application section 11. As described above, the slice sticking part 9 is provided in the vicinity of the guide rollers 91 and 92 of the carrier tape guide section 8, namely, in the vicinity of a portion where the carrier tape 21 crosses the slide transfer section 10. The slice sticking part 9 is positioned under the control of the controller 50 so that a portion (slice carrying portion) of the carrier tape 21 where the sliced specimen is carried is located at a specific position in the middle of the guide rollers 91 and 92, and the carrier tape sandwiched between the guide rollers 91 and 92 of the guide section 8 is pressed against the slide 22-3, to transfer the sliced specimen 24 carried by the carrier tape 21 to the slide 22-3. Specifically, as described above, the sliced specimen 24 is moved to the slide 22-3 side with the carrier tape 21 sandwiched between the guide rollers 91 and 92. In addition, as a modification, there may be provided one or more pushers (not shown) that operate so as to press the carrier tape 21 against the lower side from the side on which the sliced specimen 24 is not carried. When a plurality of pushers are used, they can be arranged at, e.g., a position corresponding to the sticking position of the sliced specimen on the slide (see FIG. 6).

The spreading section 12 extends along the X-axial direction on the terminal end of the slide transfer section 10, and transfers the slide with the thin slice in the X-axial direction. The spreading section 12 is a member for sending the slide 22 with the thin slice to the slide return section 13 from the slide transfer section 10, wherein the slide 22 with the thin slice is heated during the transfer of this slide to stretch the tissue of the sliced specimen 24 and strengthens adhesiveness between the sliced specimen 24 and the slide 22. Namely, the heater 61 is provided in the spreading section 12, so that the slide is heated to a predetermined temperature (such as about 40° C. to 60° C., for several seconds to several tens of seconds), for example.

In order to longitudinally transfer the slide with the thin slice, the spreading section 12 includes an operation piece 49 for pushing out a short-directional end portion of the slide and a motor 47 for driving the operation piece 49. The motor 47 can be driven so as to reciprocatively move two connection bars 48 connecting to the operation piece 49, wherein the slide 22 with the thin slice transferred from the slide transfer section 10 is locked in a state where the connection bars 48 are most extended, and the slide is transferred to a position capable of being supplied to the slide return section 13 in a state where the connection bars are made shortest (position shown at 49-1 in FIG. 2).

The slide return section 13 extends along the Y-axial direction from the terminal end of the spreading section 12, and transfers the slide with the thin slice in an opposite direction to the slide transfer section 10 along the Y-axial direction. The slide return section 13 includes a heater 62 for keeping the heat in the slide heated by the spreading section during the transfer of the slide 22 with the thin slice. By heating and keeping the heat in the slide 22 with the thin slice by the spreading section 12 and the slide return section 13, the wrinkles of the sliced specimen 24 is stretched and sticking force of the sliced specimen 24 to the slide 22 can be strengthened.

The slide return section 13 includes a motor 53 for transferring the slide and an operation piece 52 and a motor 51 for supplying the slide from the spreading section 12. The motor 51 moves the operation piece 52 by reciprocatively moving a connection bar 54 connected to the operation piece 52. The operation piece 52 is located at a longitudinal rear end side of the slide 22 transferred by the spreading section 12 in a shortest state of the connection bar 54, and the slide is set in a state capable of being supplied to an upstream side of a conveyor belt 53 in the most extended state of the connection bar 54 (position shown at 52-1 in FIG. 2). By the movement of the slide up to the terminal end by the conveyer belt 53 of the slide return section 13, the slide 22 can be supplied to a the switch section 16.

The switch section 16 functions to switch transfer of the slide transferred by the slide return section 13 to either the returning transfer section 14 or the carrying-out section 15, and is configured by a motor capable of transferring the slide with the thin slice along the X-axial direction.

The returning transfer section 14 is configured by a motor and supplies the slide with the thin slice to the slide transfer section 10. The carrying-out section 15 is configured by a motor and carries out the slide with the thin slice to the outside.

Figure 16:
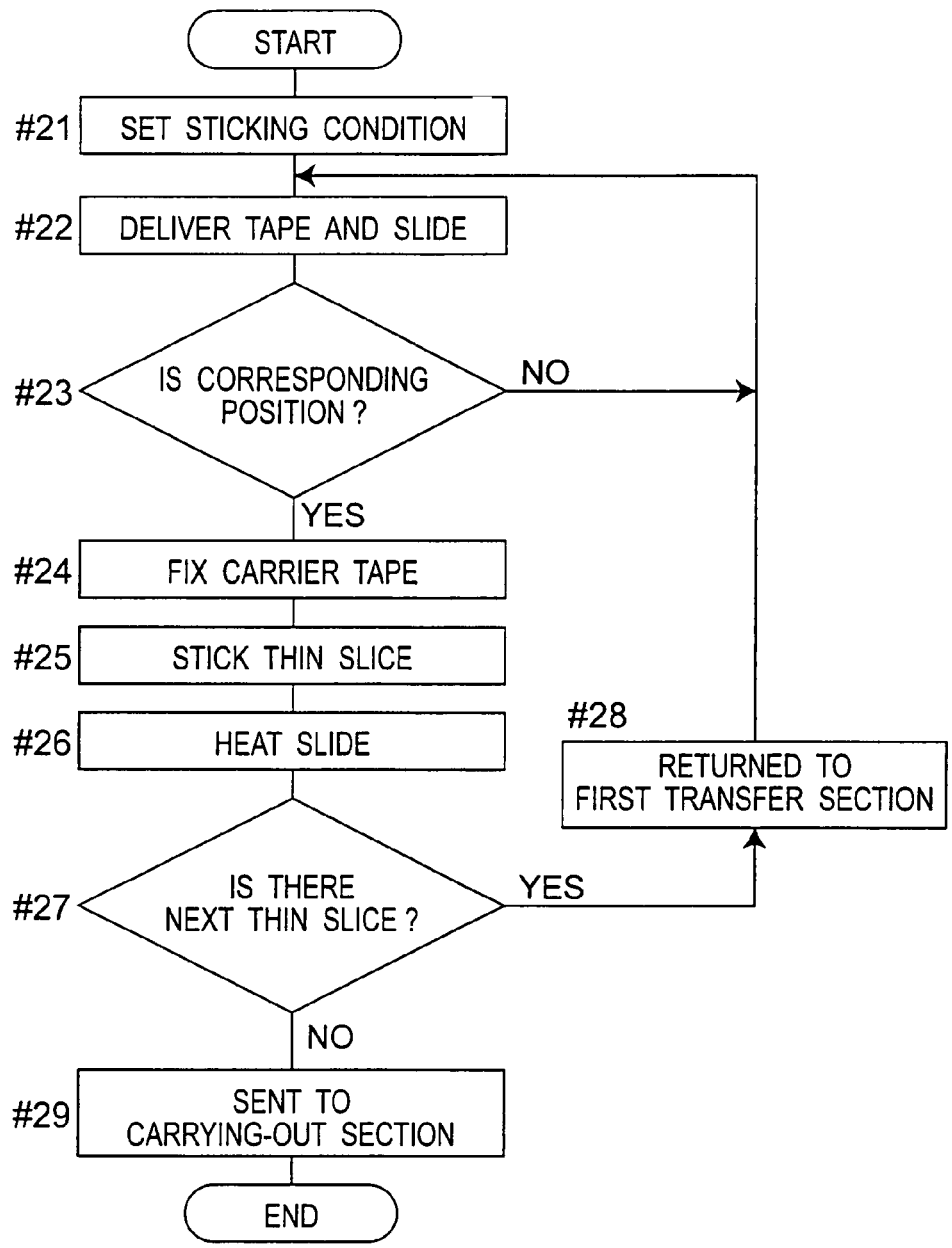
FIG. 16 is a flowchart of a processing operation for preparing a slide stuck with one sheet of thin slice.

Next, the operation of preparing the slide with the thin slice by using each member provided in the specimen sticking chamber 100B will be described in detail. FIG. 16 is a flowchart of a processing operation of preparing one sheet of slide with the thin slice. Such operation processing is performed by each of the members performing the operations as described below, by an instruction given from the controller 50.

First, sticking conditions are set in a storage area in the controller 50 by operating an input section (not shown) (#21). The sticking conditions include a thickness per one sheet of thin slice, the number of sticking of the sliced specimen per one sheet of slide, a sticking position of the sliced specimen to the slide, a heating temperature in the spreading section 12 and the slide return section 13, the number of preparing of the slides with the thin slices, and so forth. When the input of these conditions is finished, the operation as described below is started by operating a start button (not shown). Description of the slicing operation performed in the specimen preparing chamber 100A will be omitted, and only the preparing operation of the slide with the sliced specimen in the specimen sticking chamber 100B will be described.

By the slicing operation performed in the specimen preparing chamber 100A, the carrier tape 21 is transferred with the sliced specimen 24 carried on the surface of the carrier tape 21. In addition, an unused slide is supplied to the slide transfer section 10 from the slide storage section 40 simultaneously, and the slide is transferred to the sticking position of the sliced specimen along the Y-axial direction (#22). On the halfway of this transfer, the slide is stopped once at an adhesive liquid application position (position F in FIG. 2) by the adhesive liquid application section 11, and the adhesive liquid is applied by the adhesive liquid application section 11.

Figure 17:
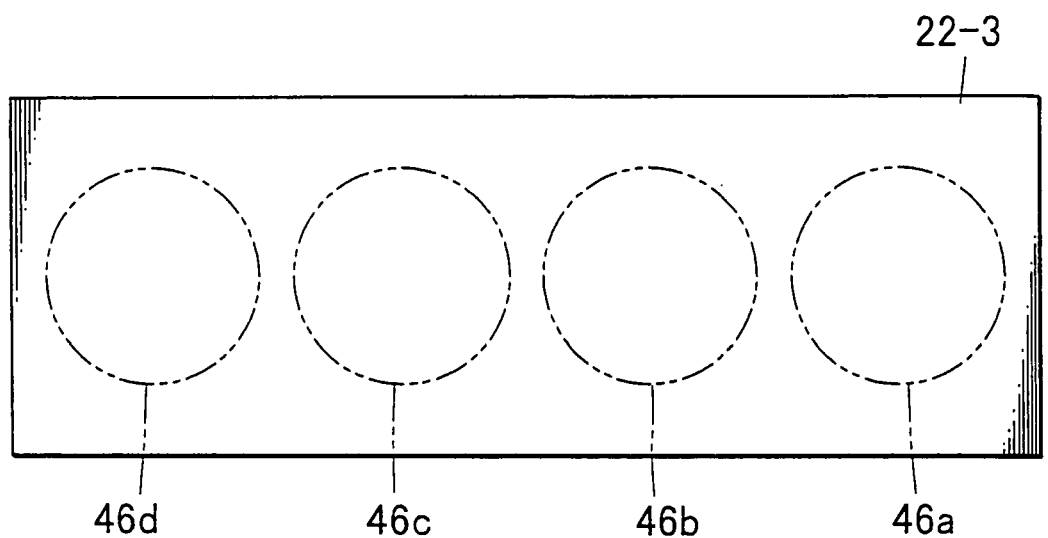
FIG. 17 is a schematic view showing an example of an application position of an adhesive liquid.

In this embodiment, description will be given below on a case where the adhesive liquid application section 11a having four nozzles shown in FIG. 15A is used. As shown in FIG. 17, an adhesive is applied to positions 46a, 46b, 46c, 46d corresponding to the four nozzles 41a, 41b, 41c, 41d on the slide stopped at the adhesive liquid application position. For example, the adhesive liquid discharged from the nozzle 41a is applied to the position 46a on the slide 22. Namely, by controlling the opening/closing of the opening/closing valves 42a, 42b, 42c, 42d of the adhesive supplying section 11a, the adhesive can be applied to any of the positions on the slide 22. In addition, when the specimen has a large size and the specimen is stuck to a position between the nozzle positions, the adhesive liquid may be discharged from a plurality of nozzles in one sticking operation (for example, by using the nozzle 41a and the nozzle 41b, the specimen is stuck to a position between the nozzle 46a and the nozzle 46b in one sticking operation).

Description will be given below on such a case taken as an example where two sliced specimens are stuck to one slide, wherein the first sliced specimen is stuck at the position 46a, and the second sliced specimen is stuck at the position 46c. Namely, when the opening/closing valve 42a is opened by the controller 50, the adhesive liquid drops from the nozzle 41a by gravitational force. As described above, a predetermined drop distance is provided between the nozzle and the surface of the slide, and therefore the adhesive liquid dropped from the nozzle 41a is diffused and applied by impinging on the surface of the slide.

After the application of the adhesive liquid is ended, the slide is transferred to the position E of sticking the sliced specimen by the slide transfer section 10, and corresponding positioning of the slide is completed.

Figure 18:
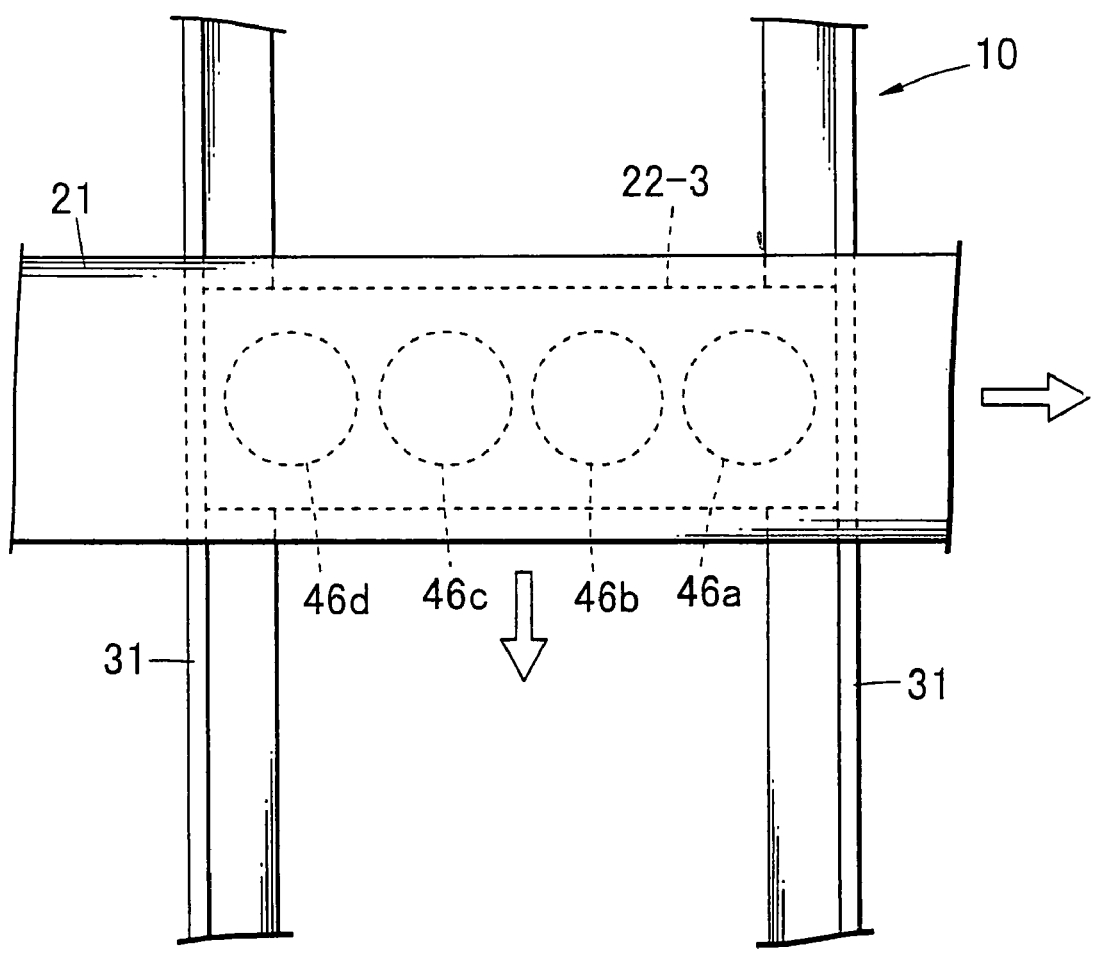
FIG. 18 is a view showing a relation between a position of sticking the sliced specimen to the slide and a transfer amount of a carrier tape.

On the upper side of the corresponding position of the slide, the carrier tape exists so as to be orthogonal thereto. Therefore, as shown in FIG. 18, by controlling the feed amount of the carrier tape 21, the sliced specimen can be moved to any position on the slide 22-3. As described above, since the adhesive liquid is applied to the position 46a, the carrier tape 21 is traveled so that the sliced specimen carried by the surface of the carrier tape 21 faces the position 46a.

When the slide 22 and the carrier tape 21 are transferred to the corresponding position (Yes in #23), the carrier tape 21 is sandwiched between the guide rollers 91 and 92, and is fixed therebetween (#24).

Subsequently, the guide rollers 91 and 92 are moved to the lower side with the carrier tape 21 sandwiched between the guide rollers 91 and 92, the sliced specimen 24 carried by the carrier tape 21 is pressed against the adhesive liquid on the upper surface of the slide 22, and the sliced specimen 24 is transferred from the carrier tape 21 to the slide 22, by the operation of the slice sticking part 9 (#25).

The slide 22 with the thin slice, to which the sliced specimen 24 is transferred, is transferred to the spreading section 12 by the slide transfer section 10. The slide 22 with the thin slice transferred to the spreading section 12 is heated (at about 40 to 60° C., for example) by the heater 61 provided in the spreading section 12, the tissue of the sliced specimen 24 is stretched, and the sticking force of the sliced specimen 24 to the slide 22 is strengthened (#26).

Subsequently, the slide 22 with the thin slice is supplied to the slide return section 13, and is transferred in the opposite direction to the slide transfer section 10 along the Y-axial direction. The slide return section 13 is kept warm (for example, about 40° C.) by the heater 62, allowing no wrinkles to be regenerated and the adhesiveness between the sliced specimen 24 and the slide 22 is strengthened. Thus, sticking of first sheet of sliced specimen 24 is completed.

In this processing example, the second sheet of sliced specimen 24 is stuck to the same slide (#7), and therefore the slide transferred by the slide return section 13 and sent to the switch section 16 is returned to the slide transfer section through the returning transfer section 14 (#28). The same processing is performed hereunder, and the application of the adhesive liquid to the position 46c on the slide, sticking of the second sheet of sliced specimen 24 to the position 46c on the slide, heating by the spreading section 12, and heat reservation by the slide return section 13 are performed, and the slide, to which the two sheets of sliced specimens are stuck, is sent to the switch section 16.

Two sliced specimens are stuck to the slide, and there is no next sliced specimen. Therefore, the switch section 16 sends the slide to the carrying-out section 15 (#29), and the slide is ejected to the outside by the carrying-out section 15. The slide with the sliced specimen thus carried out to the outside is sent to a heat reserving cabinet or the like, and preferably the adhesive liquid is completely evaporated.

Thus, preparation of one sheet of slide with the thin slice is finished, and the aforementioned operations are repeatedly performed until the slides of a predetermined number inputted by the input section are prepared.

As described above, according to the sliced specimen preparing apparatus of this embodiment, by providing the slide return section 13 that returns the slide, to which the sliced specimen is stuck, to the slide transfer section, the returning transfer section 14, and the switch section 16, a plurality of sliced specimens can be stuck to one sheet of slide. In addition, when the second sheet of sliced specimen is stuck to the slide, the transfer direction of the carrier tape is aligned to a direction crossing the slide transfer section 10 so as to accurately control the sticking position, and the adhesive liquid application section that applies the adhesive liquid is configured such that the adhesive liquid can be applied at any position on the slide 22, thereby making it possible to stick a plurality of sliced specimens to the slide even more securely.

Figure 19:
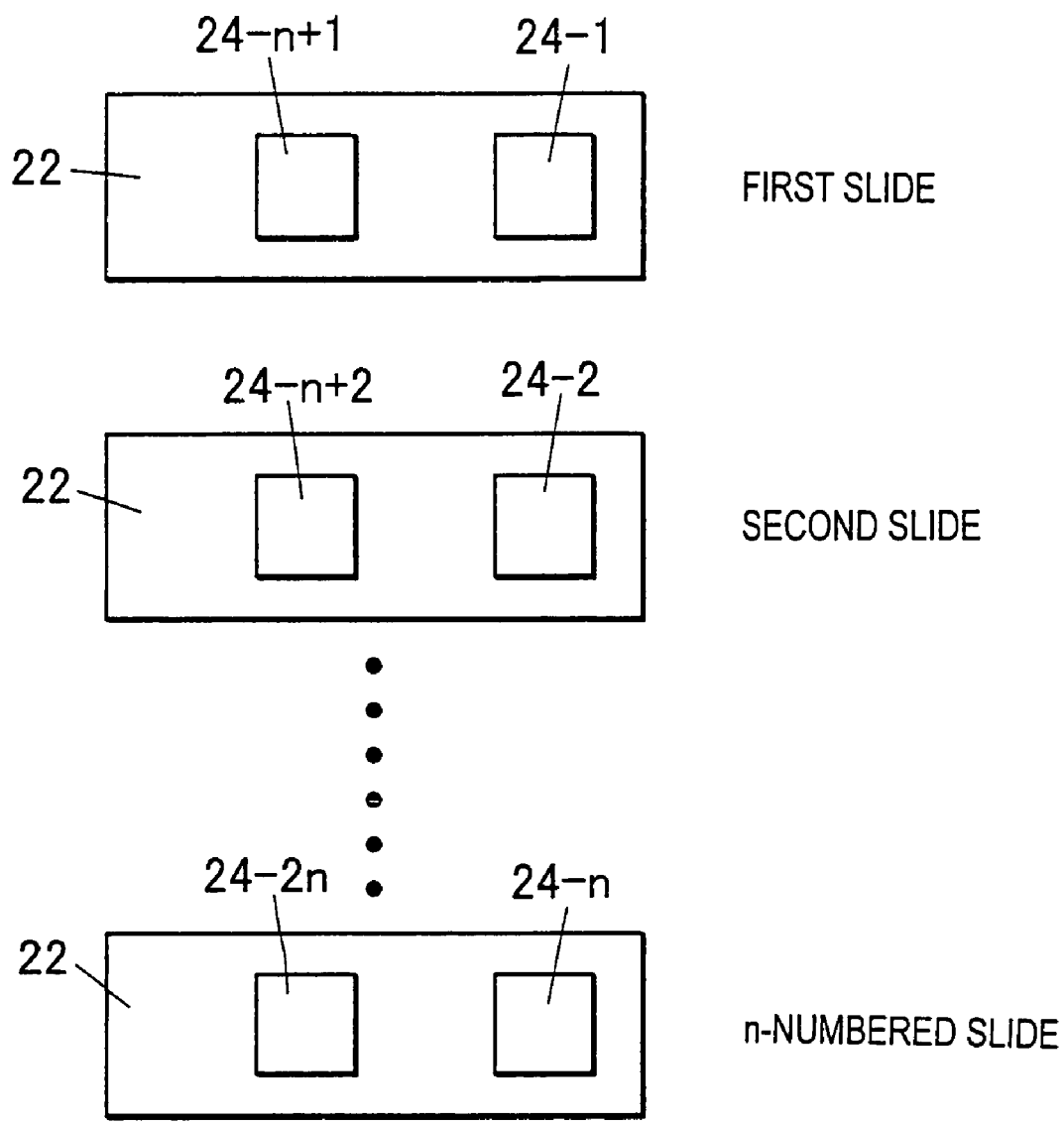
FIG. 19 is an explanatory view showing a modified example of an order of sticking the sliced specimen to the slide.

According to the aforementioned embodiment, the operation processing is performed so that continuously sent sliced specimens are stuck to one sheet of slide. However, the present invention is not limited thereto. Namely, as shown in FIG. 19, sequentially sent sliced specimens (24-1, 24-2, ..., 24-n) are sequentially stuck to a first position on an unused slide, and then after the sliced specimen is stuck to all the slides of a predetermined number of sheets (n-sheets), sliced specimens (24-n+1, 24-n+2, ..., 24-2n) may be stuck to a second position of the slide. Note that the slide, to which the first sheet of sliced specimen is stuck at this time, is preferably placed in stock on the conveyor belt of the slide return section 13.

When the adhesive liquid application section 11b with structure shown in FIG. 15B is used as the adhesive liquid application section 11, the application of the adhesive liquid is performed so that misty adhesive liquid is discharged at wide angles. Thus, the application is performed over the entire surface of the slide by one discharge.

In addition, according to the sliced specimen preparing apparatus of the present invention, by using the surface leveling sensor 60, the face preparation for the top face of the specimen block can be performed by a simple processing, and the inclination angle in the X-axial direction can be set at any value. Further, since the face preparation is performed in a non-contact state with the specimen block, no defect in the specimen block occurs and no hygienic problem occurs. In addition, since the inclination angle of the surface of the specimen block can be set at any angle, the cutting surface for preparing the sliced specimen and the inclination angle of the surface of the specimen block can be made parallel to each other. Thus, the specimen sliced in parallel to the surface of the specimen block can be prepared.

In the above embodiment, the surface leveling sensor 60 is provided in the vicinity of the first charger. However, the present invention is not limited thereto. For example, the surface leveling sensor 60 may be provided in the vicinity of the cutter section, and can be shared with the sensor for the height position adjustment of the specimen block used in the slicing operation.

The sliced specimen preparing apparatus according to the present invention is used in physical and chemical sample analysis, microscopic observation of a biotic sample, and the like.

It is noted that by suitably combining any embodiments out of the above-described various embodiments, advantages of each embodiment can be provided.

Although the present invention is sufficiently described in conjunction with the preferred embodiments with reference to the attached drawings, various changes and modifications are apparent to those skilled in the art. Such changes and modifications is interpreted as being included in the scope of the present invention as defined in the appended claims without departing therefrom.

What is claimed is:

1. A sliced specimen preparing apparatus comprising:
   a specimen block transfer section that adjusts a height position of a specimen block and transfers the specimen block;
   a cutter section having a cutter and a blade, wherein the cutter is movable in an extending direction of the blade;
   a detector that detects a position of the blade of the cutter in a direction orthogonal to a transfer direction of the specimen block;
   a carrier tape guide section that carries and moves a thin slice of the specimen block sliced by the cutter on a surface of a carrier tape;
   a slice sticking part that makes a portion of the carrier tape that carries the thin slice come close to a surface of a slide and thereby allows the thin slice carried by the carrier tape to be transferred onto the surface of the slide; and
   an operation controller that controls the specimen block transfer section, the cutter section, the detector, the carrier tape guide section, and the slice sticking part for continuously preparing the sliced specimen, wherein the operation controller prepares the thin slice by automatically and continuously slicing a surface layer portion of the specimen block by the cutter and transfers the thin slice to the slide,
   wherein the operation controller further controls the relative movement of the specimen block transfer section and the cutter of the cutter section for adjusting the surface layer portion of the specimen block to obtain the thin slice;
   wherein the operation controller further controls the height position of the specimen block to a cutting surface after the slicing of the specimen block to a next sliceable position, such that the slicing operation is continuous;
   wherein the cutter is moved in the extending direction of the blade every time a previously set number of times of the slicing operation is completed, such that the cutter firstly contacts at a contacting area of a blade edge of the cutter with the specimen block after the adjustment of the height position is sequentially changed, and thereafter the height position of the blade edge of the cutter after the change in a thickness direction of the blade is measured by the detector, and
   based on the measurement information of the detector, the sliceable position is corrected and aligned to a position apart from the height position of the blade edge of the cutter after the change, by a thickness of the sliced specimen in the thickness direction of the blade, and then the slicing operation is resumed.

2. The sliced specimen preparing apparatus according to claim 1, wherein
   the cutter section includes a nozzle for discharging compressed air toward the blade edge of the cutter and an air supply section for supplying the compressed air to the nozzle; and
   the operation controller controls that the blade edge of the cutter is blown by the compressed air, the blade edge of the cutter contacting the specimen block after preparing the sliced specimen by the cutter, in each of the slicing operation.

3. A sliced specimen preparing apparatus, comprising:
   a transfer section that transfers a specimen block mounted on a block placement table in an X-axial direction, the block placement table moves at an inclination angle of a specimen block having a flat and smooth top face relative to an XY orthogonal two-axial directions and a Z-axis directional height position;
   a line sensor located in a transfer route of the block placement table by the transfer section, the line sensor comprising a projector and a light receiver disposed opposite to each other in the Y-axial direction and emitting light having a width in a Z-axial direction;
   a cutter extends in the Y-axial direction to slice a surface layer portion of the specimen block transferred in the X-axial direction by the transfer section;
   a carrier tape guide section for moving a thin slice of the specimen block sliced by the cutter while carrying the thin slice on a surface of a carrier tape;
   a slice sticking part that makes a portion of the carrier tape that carries the thin slice come close to a surface of a slide and thereby allows the thin slice carried by the carrier tape to be transferred onto the surface of the slide; and
   an operation controller that controls the specimen block transfer section, the cutter section, the detector, the carrier tape guide section, and the slice sticking part for automatically and continuously slicing the surface layer portion of the specimen block by the cutter, and transferring the sliced surface layer portion onto the slide to continuously prepare a sliced specimen;

wherein the operation controller controls the transfer section to move approximately in a X-axis directional intermediate position of the specimen block to align with a set position of the line sensor;

wherein the operation controller further detects a received light amount from the line sensor and adjusts an inclination direction of the block placement table in the Y-axial direction to fix the Y-axis directional inclination angle of the specimen block at an angle at which the received light amount of the line sensor becomes maximum;

wherein the operation controller controls the transfer section to move the block placement table back and forth in the X-axial direction by a predetermined amount to detect the received light amount from the line sensor at that position, and further controls the X-axis directional inclination angle of the specimen block that the operation controller calculates based on the predetermined amount of movement of the specimen block in the X-axial direction and the information on the received light amount from the line sensor at each position, and the inclination angle of the block placement table is adjusted such that the calculated X-axis directional inclination angle makes a predetermined angle with respect to an XY plane.

4. The sliced specimen preparing apparatus according to claim 3, wherein after the operation controller moves the transfer section in the approximately X-axis directional intermediate position of the specimen block to align with the set position of the line sensor, and before the inclination direction of the specimen block is adjusted in the Y-axial direction, the operation controller further moves the transfer section in a height position of the block placement table in the Z-axial direction such that the received light amount of the line sensor is set to be a predetermined amount by light shielding by the specimen block.

5. The sliced specimen preparing apparatus according to claim 3, wherein the operation controller adjusts the inclination angle of the transfer section such that the calculated X-axis directional inclination angle is parallel to the XY plane.

6. A sliced specimen preparing apparatus for sticking a thin slice obtained by slicing a surface layer portion of a specimen block and transferred while being adsorbed on a carrier tape, to a slide to which an adhesive liquid is applied, the apparatus comprising:

a slide supply section capable of storing the slide in an unused state and carrying out the slide one by one;

a first transfer section extending from the slide supply section in a direction crossing a traveling track of the carrier tape;

an adhesive liquid application section for applying the adhesive liquid onto a predetermined position of the slide, at a place on the first transfer section located between a sticking position, to which the thin slice is stuck, on the slide transferred by the first transfer section and the slide supply section;

a slice sticking part for making the thin slice transfer onto the slide by performing alignment such that the thin slice adsorbed on the carrier tape is made to face the sticking position on the slide transferred by the first transfer section, and by making the carrier tape come into contact with the slide;

a second transfer section provided in parallel to the first transfer section, for transferring the slide transferred by the first transfer section in an opposite direction to the transfer direction of the first transfer section;

a returning transfer section provided in communication with the second transfer section, for supplying the slide transferred by the second transfer section to the first transfer section again;

a carrying-out section provided in communication with the second transfer section, for carrying out the slide transferred by the second transfer section to the outside of the apparatus;

a switch section for switching the transfer direction of the slide transferred by the second transfer section toward one of the returning transfer section and the carrying-out section; and wherein an operation controller controls the first transfer section, the second transfer section, the returning transfer section, the carrying-out section and the switch section.

7. The sliced specimen preparing apparatus according to claim 6, wherein the second transfer section includes a heating and heat reserving section for heating and heat-preserving the slide.

8. The sliced specimen preparing apparatus according to claim 6, wherein the adhesive liquid application section includes a spray nozzle for applying the adhesive liquid in a misty state onto the slide transferred by the first transfer section.

9. The sliced specimen preparing apparatus according to claim 6, wherein the adhesive liquid application section includes an adhesive liquid storage tank storing the adhesive liquid, and a drop nozzle for dropping the adhesive liquid onto the slide provided at a position lower than the adhesive liquid storage tank, and the adhesive liquid application section is provided on an upper side of the first transfer section with a drop distance secured such that a droplet dropped from the drop nozzle impinges on the slide and is diffused.

* * * * *